US008914090B2

(12) United States Patent
Jain et al.

(10) Patent No.: US 8,914,090 B2
(45) Date of Patent: Dec. 16, 2014

(54) IMPLANTABLE BIOSENSOR AND METHODS OF USE THEREOF

(75) Inventors: Faquir Jain, Storrs, CT (US); Fotios Papadimitrakopoulos, Vernon, CT (US); Diane Burgess, Storrs, CT (US); Daniel H. Grantham, Glastonbury, CT (US); Deborah G. Grantham, legal representative, Ithaca, NY (US)

(73) Assignee: The University of Connecticut, Farmington, CT (US)

( * ) Notice: Subject to any disclaimer, the term of this patent is extended or adjusted under 35 U.S.C. 154(b) by 1546 days.

(21) Appl. No.: 11/862,866

(22) Filed: Sep. 27, 2007

(65) Prior Publication Data

US 2008/0154101 A1 Jun. 26, 2008

Related U.S. Application Data

(60) Provisional application No. 60/827,104, filed on Sep. 27, 2006.

(51) Int. Cl.
*A61B 5/05* (2006.01)
*A61B 5/1486* (2006.01)
*A61B 5/145* (2006.01)
*A61B 5/1459* (2006.01)
*A61B 5/00* (2006.01)

(52) U.S. Cl.
CPC ............ *A61B 5/0031* (2013.01); *A61B 5/14865* (2013.01); *A61B 5/14532* (2013.01); *A61B 5/14539* (2013.01); *A61B 2560/0219* (2013.01); *A61B 5/1459* (2013.01); *A61B 5/14546* (2013.01); *A61B 5/0017* (2013.01)
USPC ............ 600/345; 600/347; 600/309; 600/354

(58) Field of Classification Search
USPC .......................... 600/345, 348, 354, 347, 309; 204/403.01; 435/288.7
See application file for complete search history.

(56) References Cited

U.S. PATENT DOCUMENTS 3,672,352 A * 6/1972 Summers ...................... 600/476
4,983,181 A 1/1991 Civerchia
(Continued)

FOREIGN PATENT DOCUMENTS

WO 0030532 A1 6/2000
WO 0030698 A1 6/2000

OTHER PUBLICATIONS

International Search Report and Written Opinion; International Application No. PCT/US2007/021042; International Filing Date Sep. 27, 2007; Date of Mailing Feb. 13, 2008; 14 pages.

(Continued)

*Primary Examiner* — Michael Kahelin
*Assistant Examiner* — Tho Tran
(74) *Attorney, Agent, or Firm* — Cantor Colburn LLP

(57) ABSTRACT

Disclosed herein is an analyte sensing device capable of continuously monitoring metabolic levels of a plurality of analytes. The device comprises an external unit, which, for example, could be worn around the wrist like a wristwatch or could be incorporated into a cell phone or PDA device, and an implantable sensor platform that is suitable, for example, for implantation under the skin. The external device and the internal device are in wireless communication. In one embodiment, the external device and the internal device are operationally linked by a feedback system. In one embodiment, the internal device is encapsulated in a biocompatible coating capable of controlling the local tissue environment in order to prevent/minimize inflammation and fibrosis, promote neo-angiogenesis and wound healing and this facilitate device functionality.

40 Claims, 22 Drawing Sheets

(56) References Cited

U.S. PATENT DOCUMENTS

| | | | |
|---|---|---|---|
| 4,994,081 A | | 2/1991 | Civerchia et al. |
| 5,684,523 A | * | 11/1997 | Satoh et al. .................. 347/247 |
| 5,704,354 A | * | 1/1998 | Preidel et al. ................ 600/347 |
| 5,910,851 A | * | 6/1999 | Flaherty .......................... 398/36 |
| 6,049,727 A | * | 4/2000 | Crothall ........................ 600/310 |
| 6,565,509 B1 | | 5/2003 | Say et al. |
| 6,926,670 B2 | | 8/2005 | Rich et al. |
| 2001/0043379 A1 | * | 11/2001 | Bloom et al. ................. 359/152 |
| 2002/0030206 A1 | * | 3/2002 | Takimoto et al. ............. 257/292 |
| 2003/0044354 A1 | * | 3/2003 | Carpenter et al. ........... 424/9.51 |
| 2003/0078499 A1 | * | 4/2003 | Eppstein ....................... 600/439 |
| 2003/0099682 A1 | * | 5/2003 | Moussy et al. ................ 424/423 |
| 2004/0259270 A1 | * | 12/2004 | Wolf .............................. 436/518 |
| 2005/0021108 A1 | * | 1/2005 | Klosterman et al. ............ 607/48 |
| 2005/0070989 A1 | * | 3/2005 | Lye et al. ........................ 623/1.4 |
| 2005/0107870 A1 | * | 5/2005 | Wang et al. ................... 623/1.44 |
| 2005/0173694 A1 | * | 8/2005 | Mawst et al. .................... 257/14 |
| 2005/0187488 A1 | | 8/2005 | Wolf |
| 2005/0221276 A1 | * | 10/2005 | Rozakis et al. .................... 435/4 |
| 2006/0004272 A1 | * | 1/2006 | Shah et al. ..................... 600/365 |
| 2006/0013851 A1 | * | 1/2006 | Giroux .......................... 424/423 |
| 2006/0064037 A1 | * | 3/2006 | Shalon et al. ................. 600/586 |
| 2006/0078540 A1 | * | 4/2006 | Warren et al. ................ 424/93.1 |
| 2006/0173259 A1 | | 8/2006 | Flaherty et al. |
| 2006/0188546 A1 | * | 8/2006 | Giroux .......................... 424/426 |

OTHER PUBLICATIONS

Fischer, et al; "Assessment of Subcutaneous Glucose Concentration: Validation of the Wick Technique as a Reference for Implanted Electrochemical Sensors in Normal and Diabetic dogs"; Diabetologia; 30; pp. 940-945; (1987).

Galeska, et al; "Characterization and Biocompatibility Studies of Layer-by-Layer Self-Assembled Humic Acid/Fe3+ Films"; Materials Research Society Symposia Proceedings; 662; pp. NN4.7.1-NN4.7.6; (2001).

Lvov, et al; "Assembly of Multicomponent Protein Films by Means of Electrostatic Layer-by-Layer Adsorption"; J. Am. Chem. Soc.; 117; pp. 6117-6123; (1995).

Reach, et al; "Can Continuous Glucose Monitoring Be Used for the Treatment of Diabetes?"; Analytical Chemistry; 64; pp. 381 A-386 A; (1992).

Shichiri, et al; "Long-Term Application of Wearable Artificial Endocrine Pancreas—Closed-Loop Intravenous VS Subcutaneous Insulin Infusion"; Life Support Systems: The Journal of the European Society for Artificial Organs; 3; pp. 583-587; (1985).

Shichiri, et al; "Wearable Artificial Endocrine Pancreas With Needle-Type Glucose Sensor"; The Lancet; pp. 1129-1131; (Nov. 20, 1982).

Tsung, et al; "Preparation and Characterization of Gelatin Surface Modified PLGA Microspheres"; AAPS PharmSci; 3; pp. 1-11; (2001).

Barrett; "Resistance to Nonspecific Protein Adsorption by Poly(vinyl alcohol) Thin Films Adsorbed to a Poly (styrene) Support Matrix Studied Using Surface Plasmon Resonance"; Anal. Chem.; 73; pp. 5232-5239; (2001).

Burgess, et al; "Assuring Quality and Performance of Sustained and Controlled Release Parenterals: Workshop Report"; AAPS PharmSci; 4; Article 7; pp. 1-11; (2002).

Galeska, et al; "Calcification-Resistant Nafion/Fe3+ Assemblies for Implantable Biosensors"; Biomacromolecules; 1; pp. 202-207; (2000).

Galeska, et al; "Characterization and Biocompatibility Studies of Novel Humic Acids Based Films as Membrane Material for an Implantable Glucose Sensor"; Biomacromolecules; 2; pp. 1249-1255; (2001).

Gerritsen, et al; "Performance of Subcutaneously Implanted Glucose Sensors for Continuous Monitoring"; The Netherlands Journal of Medicine; 54; pp. 167-179; (1999).

Hickey, et al; "Dexamethasone/PLGA Microspheres for Continuous Delivery of an Anti-Inflammatory Drug for Implantable Medical Devices"; Biomaterials; 23; pp. 1649-1656; (2002).

Hickey, et al; "In Vivo Evaluation of a Dexamethasone/PLGA Microsphere System Designed to Suppress the Inflammatory Tissue Response to Implantable Medical Devices"; Journal of Biomedical Materials Research; 61; pp. 180-187; (2002).

Kerner; Implantable Glucose Sensors: Present Status and Future Developments; Exp Clin Endocrinol Diabetes; 109; Suppl 2; pp. S341-S346; (2001).

Kim, et al; "Characterization of Zirconium Phosphate/Polycation Thin Films Grown by Sequential Adsorption Reactions"; Chem. Mater.; 9; pp. 1414-1421; (1997).

Kim, et al; "Pharmacokinetic Characterization of 14C-Vascular Endothelial Growth Factor Controlled Release Microspheres Using a Rat Model"; Journal of Pharmacy and Pharmacology; 54; pp. 897-905; (2002).

Kim, et al; "Formulation and Release Characteristics of Poly(lactic-co-glycolic Acid) Microspheres Containing Chemically Modified Protein"; Journal of Pharmacy and Pharmacology; 53; pp. 23-31; (2001).

Koschinsky, et al; "Sensors for Glucose Monitoring: Technical and Clinical Aspects"; Diabetes/Metabolism Research and Reviews; 17; pp. 113-123; (2001).

Mercado, et al; "In Vitro and In Vivo Mineralization of Nafion Membrane Used for Implantable Glucose Sensors"; Biosensors & Bioelectronics; 13; pp. 133-145; (1998).

Tsung, et al; "Preparation and Stabilization of Heparin/Gelatin Complex Coacervate Microcapsules"; Journal of Pharmaceutical Sciences; 86; pp. 603-607; (1997).

Turner, et al; "In Vitro Diagnostics in Diabetes: Meeting the Challenge"; Clinical Chemistry; 45; pp. 1596-1601; (1999).

Wang; "Glucose Biosensors: 40 Years of Advances and Challenges"; Electroanalysis; 13; pp. 983-988; (2001).

* cited by examiner

Fig. 10 Top

Fig 10 Bottom Left.  Fig 10 Bottom Right.

(i) Layout of two sub-chips.

Cross section of a via and bump, top view of the pad and interconnect (ii) Cross-sectional schematic illustration of bonding between a via and a bump for sub-chips #1 and #2. (See Figure 10, Bottom Left)

IMPLANTABLE BIOSENSOR AND METHODS OF USE THEREOF

CROSS REFERENCE TO RELATED APPLICATION

This application claims priority from U.S. Provisional Application Ser. No. 60/827,104 filed Sep. 27, 2006, which is hereby incorporated by reference in its entirety.

BACKGROUND

Careful metabolic monitoring and proper treatment can improve control of metabolic diseases such as diabetes and obesity. Knowing a patient's metabolism along with other physiological parameters allows for correct dosing and delivery of medications and nutrients. Improvements in metabolic measurement technology are essential for better diagnostics and advances in treatment of metabolic diseases and conditions. Treatment of metabolic diseases and conditions ideally requires frequent and timely monitoring which drives a need for monitors that are non-invasive, real-time, portable, low cost, and accurate. Metabolic data are also useful in assessing the physiological homeostatic conditions of patients and healthy subjects in general.

Blood glucose concentration data is extremely useful for the control of metabolic diseases such as diabetes and for monitoring the overall metabolic condition of a human subject. An accurate, real-time, noninvasive method for measurement of blood glucose levels is of great interest in the diabetic community. Current technologies involving the measurement of blood glucose by drawing blood are invasive and often lead to poor patient compliance. Measurement by probe involves frequent lancing and may result in problems. An ideal non-invasive blood glucose sensor provides a continuous signal and/or a signal on demand that can be used to control devices, such as insulin pumps in closed loop feedback applications.

In recent years, two different types of metabolic internal units have been developed: non-invasive and minimally invasive. Non-invasive optical internal units depend on light penetration into the skin and spectroscopic measurement of metabolic levels; however, lack of analyte specificity remains a problem for optical internal units. Commercially available minimally invasive internal units can function only for the short term (a few days) and require frequent calibration via finger pricking. These commercially available internal units are either incapable of continuous monitoring of metabolic levels or are only suitable for use by qualified medical personnel.

Therefore, there exists a need for a minimally invasive or non-invasive metabolic internal unit suitable for use by the host that allows continuous and/or on demand monitoring of metabolic levels of specific analytes.

SUMMARY

An analyte sensing device comprises an external control unit and an implantable sensor platform in wireless optical communication, wherein the implantable sensor platform can pass though a 14 gauge or smaller bore needle. This implantable sensor platform comprises a variety of functional optoelectronic circuit blocks for wireless powering, interactive communication, programmable potentiostats interfacing with various electrochemical sensors, mode-selection, signal processing, calibration, analog to digital conversion, amplification, and optical transmission. The outer surface of this miniaturized sensor platform is coated with one or more biocompatible coatings, optionally capable of releasing a variety of drugs and tissue response modifiers. The external control unit comprises optical sources suitable for powering the implantable sensor platform, along with transmitters and receivers for transmitting and receiving optical commands to and from the implantable sensor platform. These optical signals are then converted to electrical pulses and processed by a microprocessor located in the external unit. In addition, the external unit is equipped with a miniaturized camera to assist in aligning the various optical components of the external unit with that of the implantable sensor platform.

DETAILED DESCRIPTION

Figure 1:
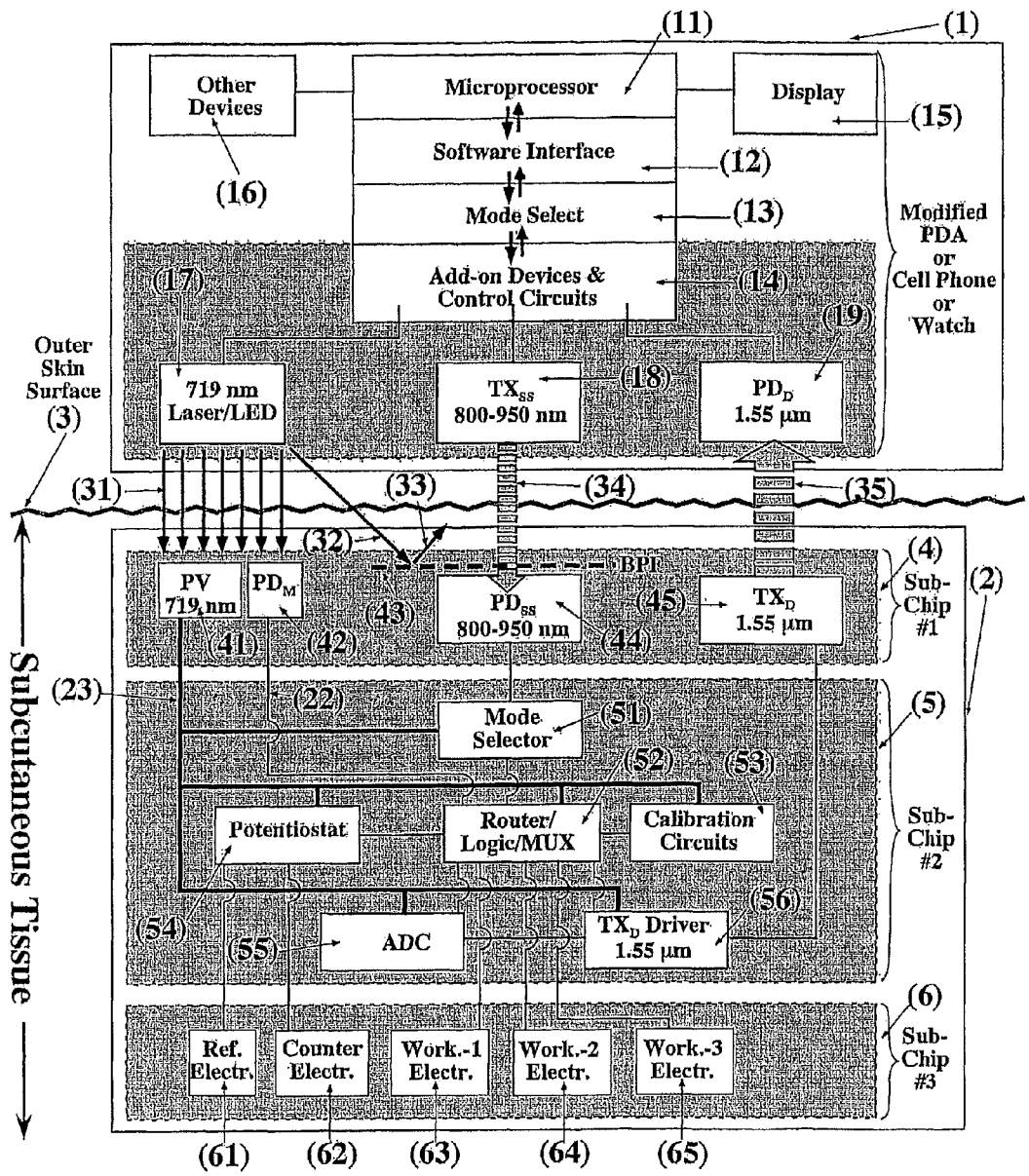
FIG. 1. Schematic representation of an embodiment of an implanted biosensor unit along with an embodiment of an external user interface unit comprising mode select, monitoring and calibration functions.

Disclosed herein is a device capable of monitoring the metabolic levels of a plurality of analytes, in a continuous or intermittent (e.g., on demand) operation. The device comprises an external unit, which, for example, is worn around the wrist like a wristwatch or carried like a Personal Digital Assistant (PDA) or a cell phone, and a sensor platform that is suitable for implantation under the skin or near the surface of another portion of a patient's anatomy. The sensor may be implantable via a needle and similarly removable via a needle, thus avoiding the need for surgical implantation and removal.

The term "analyte" refers to a substance or chemical constituent in a biological fluid (e.g., blood, interstitial fluid or urine) that can be analyzed. In one embodiment, the analyte for measurement by the devices and methods disclosed herein is glucose.

"Biocompatibility" is the ability of a material to perform with an appropriate host response in a specific application. The terms "biocompatible membrane", "biocompatible layer," and the like refer to a semipermeable membrane comprised of protective biomaterials. In one embodiment, a biocompatible membrane is a few microns thickness or more and is permeable to small-molecule analytes oxygen and glucose, but is substantially impermeable to biofouling agents (such as proteins) that could otherwise gain proximity to and possibly damage the internal unit. This "biocompatible membrane," or "biocompatible layer," may also protect the sensor from damage and inconsistency in readings resulting from inflammation and fibrous encapsulation. In some embodiments, the biocompatible membrane comprises pores (e.g., typically from approximately 0.1 to approximately 1.0 micron).

An "electrochemical sensor" is a sensor configured to detect the presence and/or measure the level of an analyte in a sample via electrochemical oxidation and reduction reactions on the sensor. These reactions are transduced to an electrical signal that can be correlated to an amount, concentration, or level of an analyte in the sample.

The sensor platform comprises one or more sensor elements. A sensor element is a component of the sensor platform that is capable of recognizing or reacting with an analyte whose presence is to be detected by the sensor platform. Typically, the sensor element produces a detectable signal after interacting with the analyte to be sensed via an electrode in the sensor platform, for example. Individual sensor elements within the sensor platform can sense the same or different analytes. In this context, the sensor platform can be adapted to measure multiple analytes simultaneously. For example, multiple individual sensor elements adapted to sense different analytes can be exposed to the external environment at the same time. Alternatively, multiple individual sensor elements adapted to sense different analytes can be exposed to the external environment at different times. Other embodiments include a sensor platform adapted to function as multi-analyte sensor on a single chip (or, alternatively, on multiple chips). In certain contexts, a signal from an individual analyte sensor element within the plurality of analyte sensor elements that contact and sense an analyte in a sensor platform are individually interrogated and/or read. Alternatively, multiple analyte sensor elements within a plurality of analyte sensor elements that contact and sense an analyte in the sensor platform are interrogated and/or read simultaneously and/or in combination.

In one embodiment, the sensor element utilizes an enzyme (e.g., glucose oxidase (GOx)) that has been combined with a second protein (e.g., albumin) in a fixed ratio (e.g., one that is typically optimized for glucose oxidase stabilizing properties) and then applied on the surface of an electrode to form a thin enzyme constituent. In one embodiment, the sensor element comprises a GOx and HSA (Human Serum Albumin) mixture. In this embodiment, the GOx reacts with glucose present in the sensing environment (e.g., the body of a mammal) and generates hydrogen peroxide, wherein the hydrogen peroxide so generated is anodically detected at a working electrode in the sensor platform.

An "electron transfer agent" is a compound that carries electrons between an analyte and a working electrode, either directly, or in cooperation with other electron transfer agents. One example of an electron transfer agent is a redox mediator.

The measurement of analytes including glucose, lactate, etc., is achieved using an external unit and an implantable biosensor platform. The external unit can provide controls for sensor unit selection and output display. In one embodiment, the device integrates sensors with biocompatible coatings as well as drug dispensing devices. In another embodiment, the device is capable of additional wireless communication with health service providers as appropriate.

The device of the present invention comprises a sensor platform and an external unit that are in operable communication through a set of transceivers. A transceiver comprises an optical transmitter and an optical receiver. In one embodiment, the optical transmitter is a light-emitting or laser diode. In another embodiment, the optical receiver is a photodetector. The two components of a transceiver are located in the external control unit (the optical transmitter) and the implanted sensor platform (the optical receiver), respectively or vise versa. The transceiver orientation is defined by the direction of transmitted light. The interactive coupling between two transceivers (transmitting in opposing directions) establishes a feedback loop via other circuits. Two transceivers with opposing location of transmitters and receivers form a closed-loop, capable of wirelessly transmitting and received commands, carrying out certain instructions as well as transmitting certain information back and forth among the two units. This interactive feedback loop enables the remote operation of the sensor platform. In addition, with the use of logic and routing circuits, the feedback loop provides multiple functionalities including initialization, calibration, and measurement of one or more analyte levels.

In one embodiment, the external unit comprises an optoelectronic receiver suitable for receiving optical pulses from the sensor platform, and converting these optical pulses to electrical pulses. In addition, the external unit contains integrated circuits suitable for processing and displaying the analyte levels that are coded in terms of pulse characteristics. An optical source located in the external unit powers a plurality of photovoltaic cells, which in turn serve as the power source for the implantable sensor platform.

In one embodiment, the sensor platform comprises a power source; one or more electrochemical sensor elements suitable for sensing of one or more analytes; one or more interfacing circuits providing operating voltages and a reference voltage to the sensor elements, wherein the interfacing circuit generates a signal proportional to the amount of analyte present; (e.g., an ultrasound transmitter) one or more signal processing circuits in operable communication with the interfacing circuit, wherein the signal processing circuit converts the analog sensor signal to digital pulses, one or more electrical to optical converters in operable communication with the signal processing circuit, wherein the electrical to optical converter converts the digital pulse to optical pulses; and a transmitter for transmitting the optical pulses to the external unit. In one embodiment, the interfacing circuit comprises a potentiostat. In one embodiment, the electrical to optical converter is an infrared (IR) transmitter suitable for the wireless relaying of analyte levels and power management information to the external unit.

In one embodiment, the sensor platform comprises three sub-chips. In one embodiment, sub-chip#1 comprises a wireless photovoltaic powering solar cell array to power all components of the sensor platform, a photodetector ($PD_M$) to monitor the power level, an infra red transmitter ($TX_D$), and a photodetector ($PD_{SS}$), along with their associated circuits. Sub-chip#1 preferably faces the portion of the external unit that serves as the power source to power photovoltaic cells (e.g., super luminescent LEDs or laser diodes). The $PD_{SS}$ puts sub-chip#1 in operable communication with sub-chip#2. For example, the photodetector ($PD_{SS}$) interfaces with a Mode Selector circuit block on sub-chip#2, which in turn communicates with Router/Logic/Mux circuits. Information regarding power levels ensures that the desired voltage and current levels are available to operate all electronic and optoelectronic circuits of internal implantable platform unit. This can prevent faulty internal unit readings due to voltage-current levels below threshold. The infrared transmitter $TX_D$ also serves to transmit information to the external unit regarding the photovoltaic power level.

Sub-chip#1 can further comprise an eye-safe infrared (IR~1.55 micrometer) InGaAsP-InP LED/laser source ($TX_D$), for example, bonded onto aSiO$_2$ coated Si substrate in the vicinity of the solar cell array. An 1.55 micrometer IR detector ($PD_D$), located in the external unit, detects the coded internal unit signal. In an alternative embodiment, the external unit further comprises a band-pass filter to reject radiation from the powering LEDs that operate in a spectral regime, which affords minimum absorption.

Sub-chip#2 comprises one or more interfacing circuits, one or more signal processing circuits, and one or more electrical to optical converters. According to one embodiment, sub-chip#2 comprises a Mode Selector and Router/MUX/Logic blocks, which interface with programmable potentiostat and calibration circuits, along with a signal processing analog-to-digital-converter (ADC) interface and $TX_D$ driver electronics. For example, once a sensor is selected, the programmable potentiostat provides appropriate voltage values for working ($V_W$), reference ($V_{REF}$), and counter ($V_C$) electrodes of the selected sensor, located on the Sub-Chip#3. The analog output of the selected sensor is thus connected (via Router/Logic/MUX block) to the potentiostat and ADC signal-processing unit. The digital output from the ADC circuit is fed to the $TX_D$ driver, which in turn is designed to interface with the infrared transmitter ($TX_D$) on sub-chip#1.

In one embodiment, the analog current developed in a glucose sensor (e.g., due to the presence of glucose in the environment adjacent to the implanted sensor platform) is converted into voltage pulses of varying width by the ADC circuit. These pulses in turn drive an infrared emitter ($TX_D$). The emitter output is received by an external photodetector ($PD_D$) located in the external unit, which can be worn on the wrist or located in a modified PDA unit. Thus, the pulse duration or frequency carries the glucose level information to the external unit, where it is processed and displayed accordingly.

Sub-chip#3 comprises one or more electrochemical sensors, for example, a glucose sensor, along with other microsensors (e.g., oxygen, pH, insulin, and ion concentration). In one embodiment, sub-chip#3 comprises an electrochemical sensor with working platinum and auxiliary platinum electrodes in an inter-digitated configuration, and a reference silver/silver chloride electrode meandering between the two platinum electrodes. Sub-chip#3 optionally comprises ionic sensors, in which field-effect transistors with an electroactive gate material coating are used.

FIG. 1 illustrates schematically an embodiment of the functional blocks of both the external control unit (1) and the sensor platform (2) subcutaneously implanted under the skin (3).

The external control unit (1) comprises a microprocessor (11), a software interface or program (12), a mode select comprising various switches (13), and various electronic and optoelectronic "Add-on Devices and Control Circuits" (14). In addition, there is a display (15) and provision for interface with "Other Devices" (16). The Add-on devices (14) include an optical source ("719 nm Laser/LED (A)) or sources at wavelengths that are not absorbed by the skin and subcutaneous tissue for powering solar cells (41) located on Sub-Chip#1 (4) of the implanted sensor platform (2). The Add-on devices (14) also includes a transmitter ($TX_{SS}$) (18), operating in the spectral range 800-980 nm, which sends optical commands as coded pulses to the $PD_{SS}$ photodetector (44), located on Sub-chip#1 (4) of the implanted sensor platform (2). The Add-on devices (14) also includes a photodetector ($PD_D$) (19) operating at 1.55 μm, which receives information as coded optical pulses from the transmitter ($TX_D$) (45) located on Sub-chip#1 (4) of the implanted sensor platform (2). An optical filter is optionally placed in front of photodetector $PD_D$ (19) in order to allow transmission of wavelengths of 1.55 μm and reject away shorter wavelength radiation.

FIG. 1 also shows an embodiment of the implantable sensor platform (2) having a compact size of 0.5 mm width×5 mm length×0.5 mm height. In this embodiment, the power source of the internal unit comprises photovoltaic (PV) solar cells (41), which are powered by high efficiency light-emitting diodes (LEDs) (17) in the external unit. These PV cells (41), operating at designed wavelength that allows transmission through the skin, provide sufficient power output (voltage and current) needed by the electronic and optoelectronic devices of the implantable sensor platform unit (2).

In this embodiment, the implantable sensor platform (2) comprises three sub-chips with the following functionality: Sub-chip#1 (4) comprises the power source (41), the power level monitor photodetector ($PD_M$) (42), the optical command receiver photodetector ($PD_{SS}$) (44) along with its band-pass filter (BPF) (43), and the transmitter ($TX_D$) (45) for transmitting the optical pulses to the external unit (1); Sub-chip#2 (5) comprises the Mode Selector circuit block (51), which interprets the optical commands from the transmitter ($TX_{SS}$) (18) to the photodetector ($PD_{SS}$) (44) and communicates it via electrical digital pulses to the Router/Logic/MUX circuit block (52). The Router/Logic/MUX circuit block (52) interfaces with the programmable Potentiostat (54), Calibration and Initialization Circuits (53), signal processing circuits (Analog-to-Digital Converter (ADC)) (55), and $TX_D$ Driver circuit (56). The Router/Logic/MUX circuit block (52) along with the programmable Potentiostat (54) interfaces with various sensor elements located on Sub-chip#3 (6); and Sub-chip#3 (6) comprises an number of electrochemical sensors, whose share the same reference (61) and counter (62) electrodes. Three working electrodes (63), (64), and (65) are explicitly shown on Sub-chip#3 (6). In alternative embodiments, the internal implantable sensor platform unit (2) comprises two sub-chips or even one chip, if integration of circuits is miniaturized further.

In operation, the implantable sensor platform unit (2) receives the powering light (31) from the optical source (17) through the skin (3). This powering light (31) is received by photovoltaic (PV) cells (41) that provide power to all devices and circuits in the implantable sensor platform (2) through bus lines (23), shown in bold. This powering light (31) is also received by the $PD_M$ photodetector (42), which provides information regarding the input power level and hence the power produced by the PV cells (41). The implantable sensor platform (2) also receives through the $PD_{SS}$ photodetector (44) optical command and control information (from the external unit via $TX_{SS}$ (18)) as pulses in a certain frequency range ($f_1$). These optical commands enable selection of various function of the implantable sensor platform such as initialization, sensor selection, calibration and measurement of analyte levels, power level check, etc. These functions are carried out by the Mode Selector (51) and Router/Logic/MUX circuit (52) blocks. These two units provide interface with all other electronic and optoelectronic and electrochemical devices and circuits within the implantable sensor platform unit (2). The $PD_{SS}$ photodetector (44) has a band pass filter (43) or a coating that blocks the incoming powering light (32) (from optical source (17)) and reflects it away (33). This prevents undesirable interference of powering light (32) with the optical pulses (34).

Once a function (e.g., initialization, sensor selection, calibration or measurement) is selected (through the microprocessor (11) and associated Software (12)), the Mode Select Unit (13) in the external control unit (1) sends encoded electrical pulses, which are transmitted optically by transmitter $TX_{SS}$ (18) to the implantable sensor platform (2) where they are received by the photodetector $PD_{SS}$ (44) and processed by the Mode Selector (51) and Router/Logic/MUX (multiplexer) block (52). Upon execution of a selected function, the result is transmitted to the $TX_D$ driver (56), which in turn powers the $TX_D$ optical transmitter (45). The $TX_D$ transmitter (45) relays the information via optical pulses (35) of a different frequency range ($f_2$) through the skin (3) to the $PD_D$ photodetector (19) located in the external unit (1). This signal is then processed by the Add-on Devices & Control Circuits (14) of the external control unit (1) in conjunction with the microprocessor (11) and the program loaded in the Software Interface (12) unit. These steps constitute a feedback loop to interactively implement a function. This loop is repeated for every function including initialization, sensor selection, calibration and measurement described below.

An exemplary initialization function operates as follows. The initialization function checks if the solar cells are receiving adequate optical power from the optical source (17). For this, the Mode Selector (51) in conjunction with the Router/Logic/MUX block (52) compares the output of the $PD_M$ photodetector (42) using a comparator with a predetermined reference, available in the Calibration Circuit unit (53). If the power level is adequate or inadequate, a signal is transmitted using the $TX_D$ driver (56) and $TX_D$ transmitter (45) to the external unit to take the appropriate action (i.e. if power is adequate proceed with the next function or if the power level is not appropriate, increase the power level of the optical source (17) via the circuits in the Add-on Devices & Control Circuits unit (14).

An exemplary sensor selection function operates as follows. The sensor selection function, a command comprising an optical pulse set is transmitted by $TX_{SS}$ (18) to the $PD_{SS}$ (44), which selects one of the three working electrodes (63, 64, and 65) shown in Sub-chip#3 (6). Once a sensor is selected, "sensor calibration" is typically performed. Sensor calibration includes configuring a programmable potentiostat (54) such that the voltage between the working electrode (63 or 64 or 65) with respect to reference electrode (61) is at the desired value dictated by the electrochemical reaction involving the detection of a certain analyte. Configuring of the potentiostat determines the appropriate voltage or current levels, as well as the mode of operation (continuous or pulsed for certain duration). This configuration is achieved by Mode Selector (51) and Router/Logic/MUX (52) circuit blocks in conjunction with the Potentiostat (54) and Calibration Circuits (53). Once the optional calibration is accomplished, the next function is sensor reading. This function is performed using potentiostat (54) and the Signal Processor & ADC block (55). The digital output of the Signal Processor & ADC block (55) is then fed to the TX$_D$ driver (56), which in turn powers the optical transmitter TX$_D$ (45). The analog electrochemical current generated by the potentiostat-driven sensor [which includes three electrodes: a working (63 or 64 or 65), a counter (62) and a reference (61)] is read, amplified, and digitized by the Signal Processor & ADC block (55). The Signal Processor & ADC block (55) converts the magnitude of the electrochemical current into digital pulses whose frequency is proportional to the analyte level. The digital electrical pulses are converted into digital optical pulses that are transmitted by TX$_D$ (45). These optical pulses (35) pass through the skin (3) and are converted back to electrical pulses by photodetector PD$_D$ (19). These electrical pulses are decoded by the external control unit (1) using the Add-on Devices and Control Circuits (14), and the analyte level is displayed on Display (15).

Changing from one sensor to another is accomplished, for example, by re-programming of the Router/Logic/MUX (52), which in turn reconfigures appropriately the Programmable Potentiostat (54). The Router/Logic/MUX (52) selects one of the desired working electrodes (63, 64, or 65). All of these commands are executed from instructions transmitted using the transmitter TX$_{SS}$ (18) and its complementary photodetector (PD$_{SS}$) (44) in the implantable sensor platform (2). Their signals are processed by the Mode Selector (51), which is interfaced to the Router/Logic/MUX (52). Router/Logic/MUX (52) performs the reconfiguration and connection to the calibration circuits. The results of calibration and comparison are fed through Router/Logic/MUX (52) to the TX$_D$ Driver (56) and Transmitter TX$_D$ (45) and relayed to the external control unit to complete the instructional set and desired function.

Figure 2:
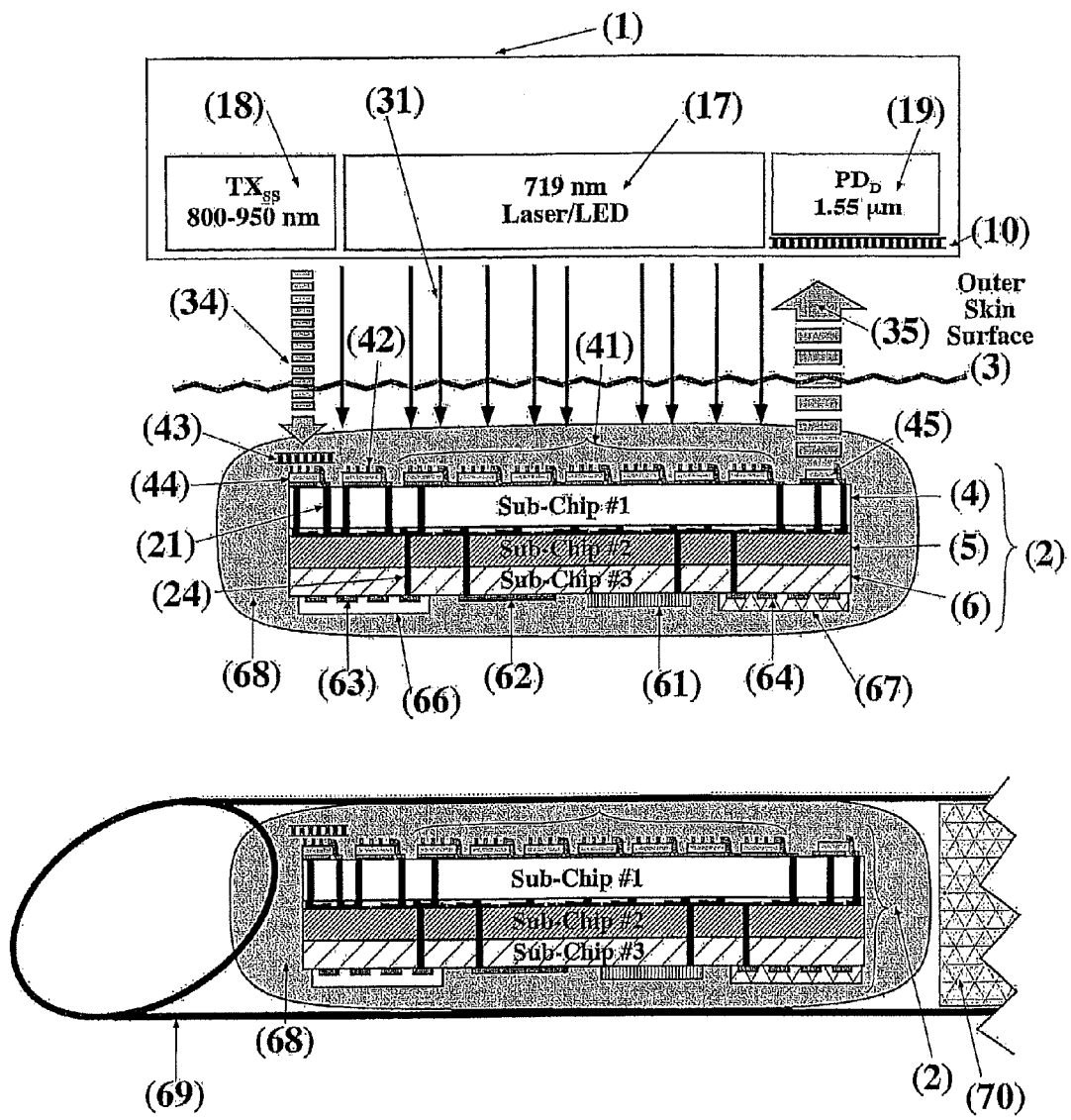
FIG. 2. Schematic representation of an embodiment of a sensor platform shown as stack of three chips encased in a suitable biocompatible coating. The sensor platform is compact enough for implantation by needle and plunger.

FIG. 2 illustrates an exemplary external control unit (1) and implantable sensor platform (2) comprising three subchips (4, 5, and 6) that are coated with a biocompatible coating (68) containing, for example, a number of tissue response modifying agents. In one embodiment, sensor platform (2) is implanted subcutaneously under the skin (3) with a hypodermic needle (69) outfitted with a plunger (70). Implantation takes place, for example, by lifting the skin up, inserting the needle containing the sensor platform (2) along with its biocompatible coating (68) and its plunger (70). After positioning the hypodermic needle (69) to the proper depth, the plunger (70) is held fixed and the needle (69) is removed, leaving the sensor platform with its biocompatible coating at the desired location. Finally the plunger is also removed. Care is exercised to ensure that the photovoltaic cells (41) are facing up towards the skin (3). FIG. 2 also schematically shows the subchip construction, interconnections and optical powering and communication interface with the external unit (1). Here, only the optical modules [laser/LED (17), TX$_{SS}$ (18) and PD$_D$ (19)] of the external control unit (1) are shown. Some interconnects are labeled (21). Working electrodes are shown with specialized coatings (66 and 67), specific to the specific analyte sensing.

Figure 3:
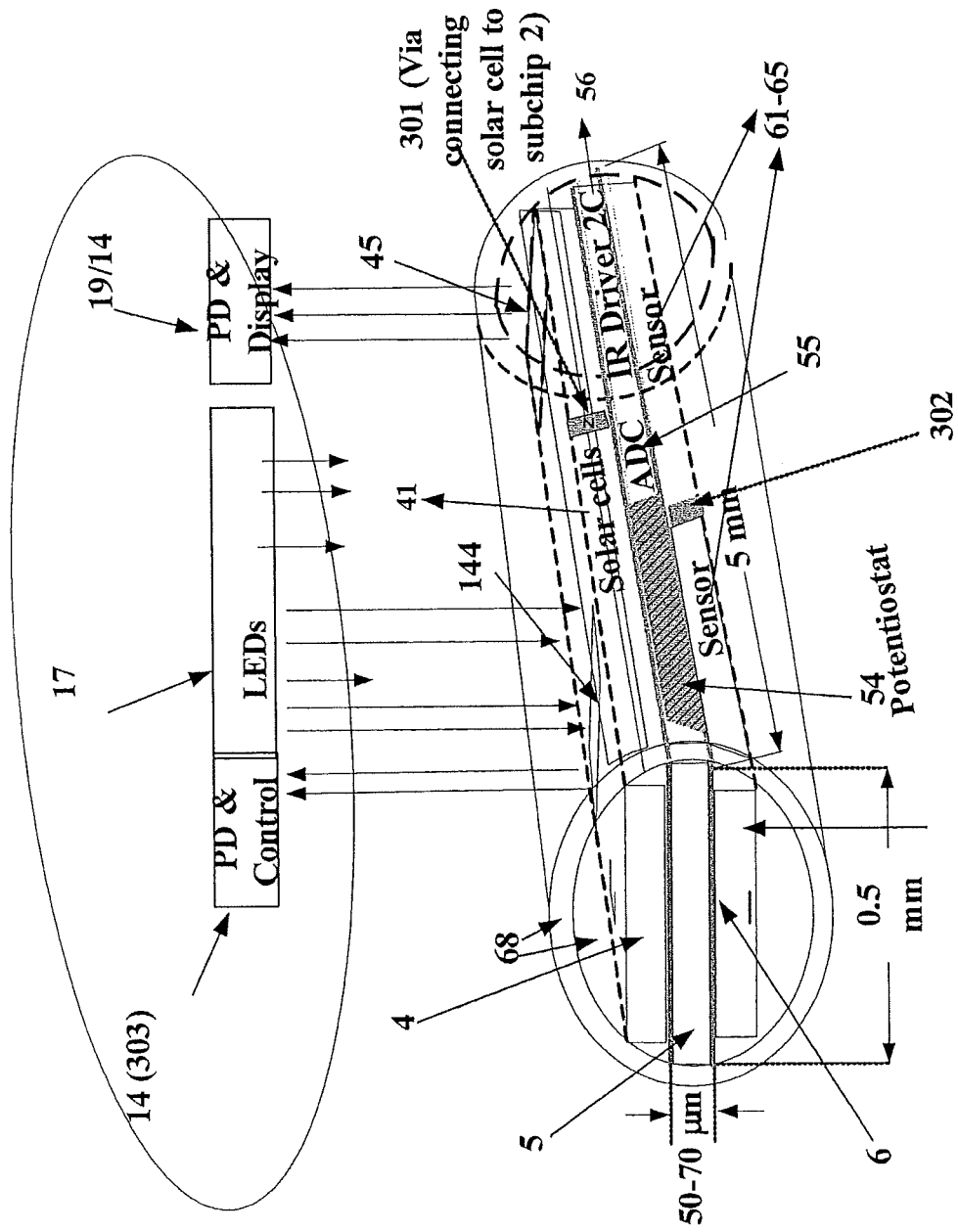
FIG. 3. Schematic view of an embodiment of a three sub-chip sensor platform along with its interface with the external control unit.
Figure 9:
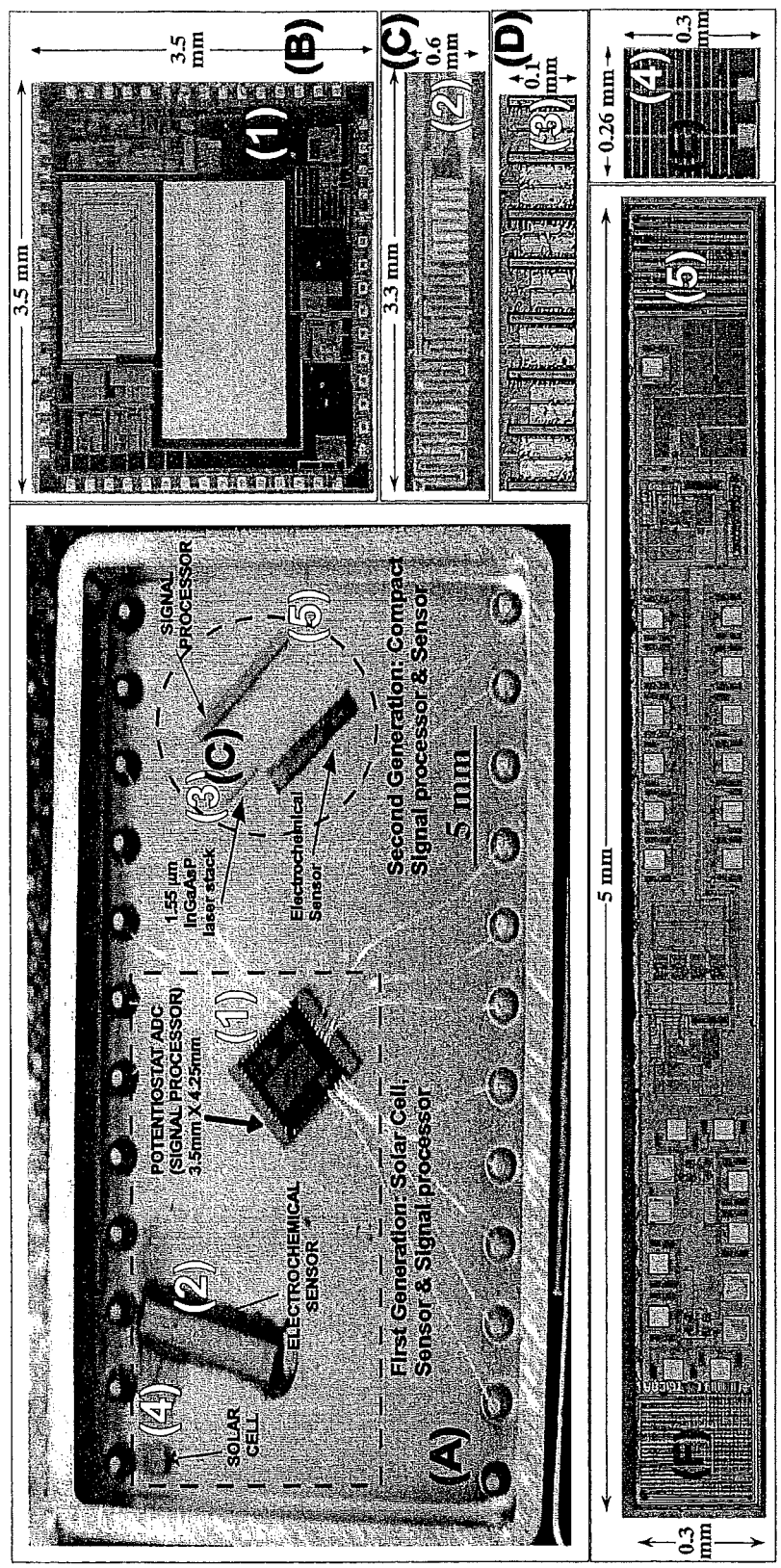
FIG. 9. Photographs showing various components of sub-chips: solar cells, laser as transmitters, signal processing chips (two generation), three-electrode electrochemical sensors.

FIG. 3 illustrates a three-dimensional (3D) schematic representation of the 0.5×5 mm implantable wireless platform, consisting of three sub-chips that are encapsulated within a biocompatible coating (34), containing a variety of tissue response modifiers (TRMs) to control, for example, tissue response and induce neo-angiogenesis. Sub-chip#3 (6) consists of an electrochemical sensor interfaced with sub-chip#2 (5) comprising a potentiostat (54), ADC (55) and IR driver (56) (for glucose transmitter TX-D (56)). Sub-chip#1 (4) includes the powering solar cells and IR transmitters. The external command, control and monitoring, modified-PDA unit is shown above the implantable sensor capsule. This unit consists of powering-LEDs (17) and photodetectors (19) for glucose level display (15) and power control circuits (14 in FIG. 1), respectively. In one design embodiment, the implantable device comprises three sub-chips, (each of about. 0.5 mm wide, 5 mm long), which are stacked on top of each other to achieve a compact configuration, suitable for needle-assisted administration (see FIG. 2). Sub-chip#1 (top) comprises the solar cells (41 in FIG. 2), photodetectors and transmitters (44) (including PD 42 shown in FIG. 2). Sub-chip#3 (6, bottom chip) comprises the three-electrode (working, reference and counter) electrochemical glucose sensor. Sub-chip #2 (5, middle) comprises a potentiostat (54), which is operably linked by vias (301 between subchip#1 and subchip#2, and 302 between subchip#2 and subchip#3; see also FIG. 10) to the electrochemical sensor (61-65 in FIG. 1) on subchip#3 and the solar cells on subchip#1 (4), generating an amperometric current that is fed to the signal-processing unit (55). This unit comprises a transconductance amplifier and an analog-to-digital (ADC) converter to convert amperometric current (i.e., glucose current) to voltage pulses. These pulses are fed to a driver (56) which in turn feeds an infra-red 1.55 µm transmitter (TX) (45) (located on sub-chip#1 (4)), using a low-power laser/LED. The optical pulses that carry glucose level information (defined as TX$_D$, D for display) are received by a photodetector (PD$_D$) (19/15) located in the external unit. [Various components of sub-chips are shown in FIG. 9].

One feature of the device is an interactive feedback system between the sensor platform and the external unit. This feedback system provides the ability to, for example; verify adequate power levels; account for other measurements such as blood pressure, body temperature, as well as factors such as pH and oxygen level, which assist to check biointernal unit calibration; and select a sensor and retrieve the information.

Figure 13:
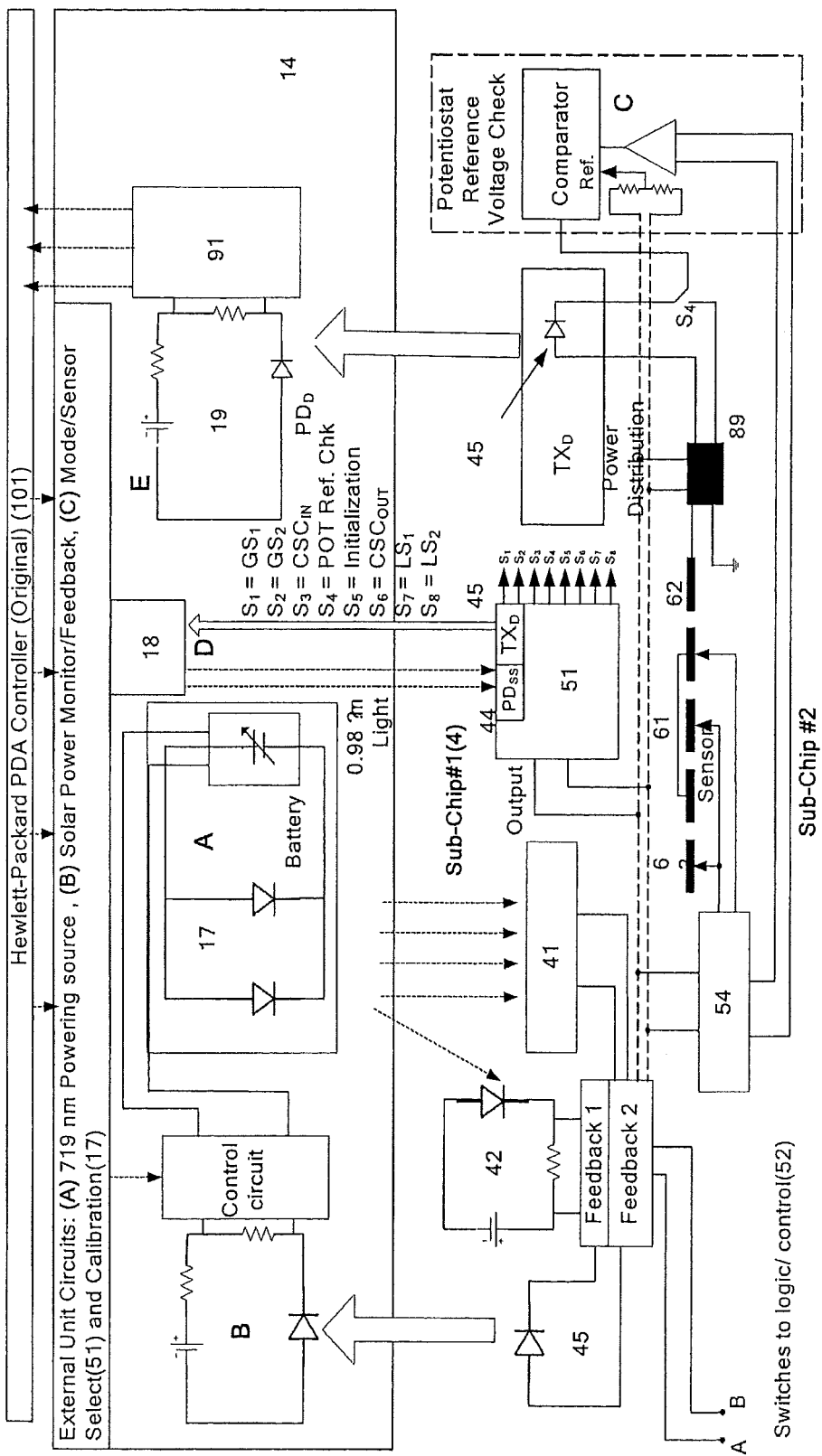
FIG. 13. Circuit schematic showing various functions of three sub-chips condensed into two sub-chips. In this version, the modified PDA unit directly communicates with the implanted unit.

For example, one feedback system provides information regarding whether the LEDs (in the external unit) are powered in a manner that ensures adequate optical input to the solar cells of the sensor platform (for details see FIG. 13). The solar cells in turn are supplying various units of the internal unit adequate voltage, current and power levels. One scheme to ensure this is to have a feedback system consisting of a photodetector (PD) monitor measuring the level of optical power received from the LEDs in the external unit (for details see FIG. 13). The PD output current is proportional to the light intensity received. This current is converted into a voltage, which compared in a comparator (COMP) against a reference. This reference may be derived from the same circuit, which supplies the reference electrode of the internal unit. The difference between the reference voltage (V$_{REF}$) and the PD derived voltage is fed to the infrared transmitter (IR-M in FIG. 3 and TX-M in FIG. 1). This signal is transmitted to the external unit. The received PD input level is compared in the CTRL unit, which in turn adjusts the power level of the LEDs.

The device can further comprise another feedback system regarding information about other measurements by the internal unit, such as blood pressure, oxygen and pH levels, which can affect the calibration or accuracy of the internal unit.

In another embodiment, the device comprises a plurality of sensors operably (operable/fluid/electrical/optical) in communication with the external unit. The operative connectivity can be provided by any communication means, such as fluid, electrical, optical, or a combination of at least one of the foregoing. The plurality of sensors can be housed within a single internal unit or multiple internal units. Once a user selects a particular sensor using the sensor select switch in the external unit, it activates an IR transmitter in the external unit. This transmitter communicates and connects to the associated photodetector (PD) shown schematically in FIG. 1 along with the block marked VDD, Vref and Control. The communication code enables the PD to interface with the potentiostat to set desired working and reference voltages needed to operate the selected sensor. In addition, the information is provided to the router switch, which physically selects the sensor and connects the potentiostat output to its terminals.

Figure 4:
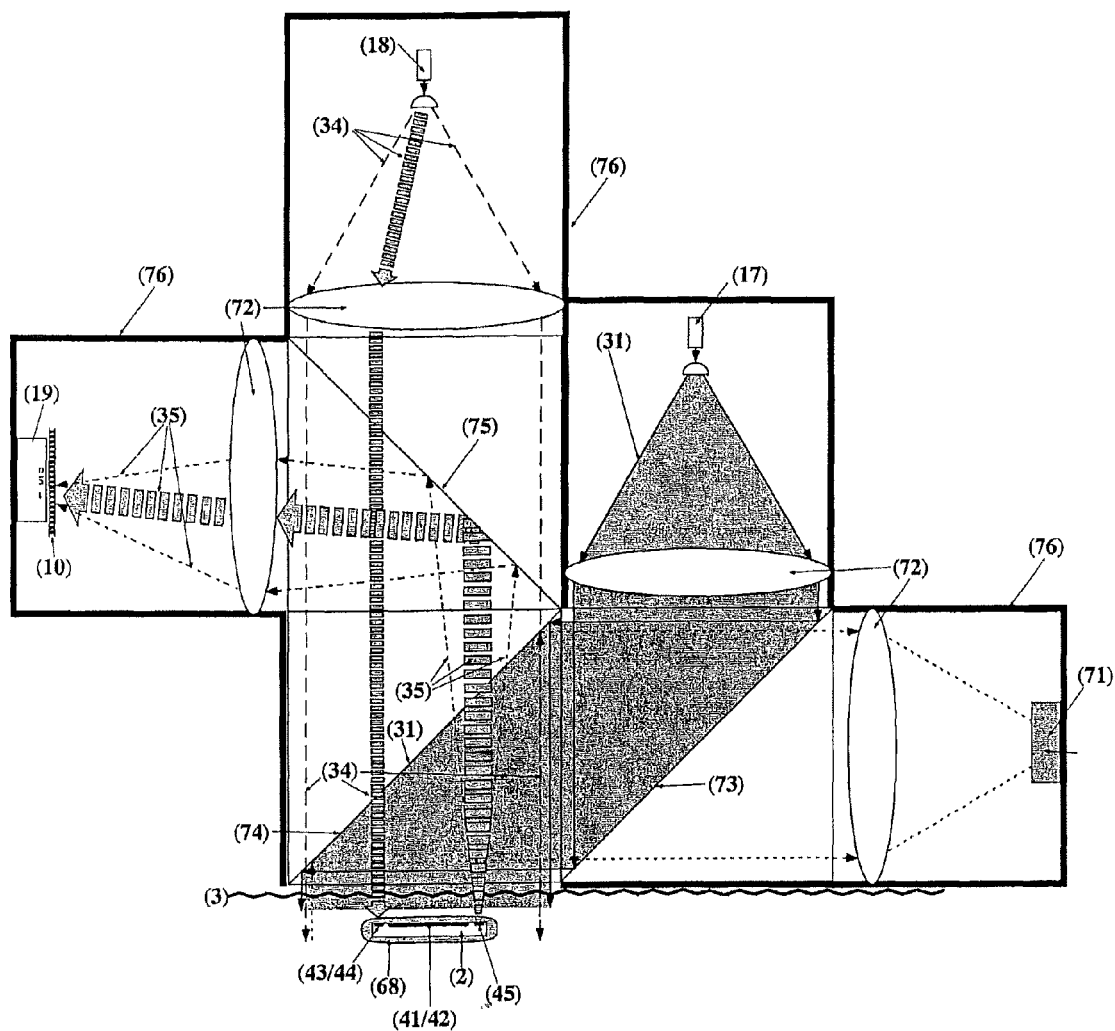
FIG. 4. Embodiment of optical and optoelectronic components housed within PDA unit and methodology to optically communicate with the implanted sensor platform.

FIG. 4 shows a schematic representation of the optical powering and communication interface located in the external control unit (1). This interface also contains a miniaturized camera (71), which assists in locating and aligning the implantable sensor platform (2) with respect to the external control unit (1). The optics elements within the external control unit (1) are housed within the casing (76) and include three cube reflectors (73, 74, and 75) equipped with the appropriate coatings to stir reflections depending to the wavelength of the radiation, along with a number of focusing lenses (72), transmitters, receivers (photodetectors) and various other beam shaping components. The light (31) from the optical powering source (17) is collimated by lens (72), steered by two cube reflectors (73 and 74) to illuminate a broad area around the sensor platform (2). This light also provides illumination for the miniaturized camera (71). The 719 nm light penetrates the skin adequately and provides enough contrast to the operator to locate and align the control unit (1) with respect to sensor platform (2). Optical commands from the $TX_{SS}$ transmitter (18) are directed through a lens (72) and two cube reflectors (75 and 74) to illuminate the similar broad area around the implanted sensor platform (2). The optical signal from the $TX_D$ transmitter (45), located in the implantable sensor platform (2) passes thought the cube reflector (74) and deflected by the mirror of the cube reflectors (75), collimated through lens (72) and detected by the photodetector $PD_D$ (19). The insertion of long wavelength pass filter (10) ensures that no interference from the 719 nm (17) and 800-950 nm (18) light sources occurs. Similarly, the band-pass filter (43) on top of the $PD_{SS}$ (44) detector in the implantable sensor platform (2) ensures no interference from the 719 nm (17) and the 1.55 μm (45) sources, respectively.

Figure 5:
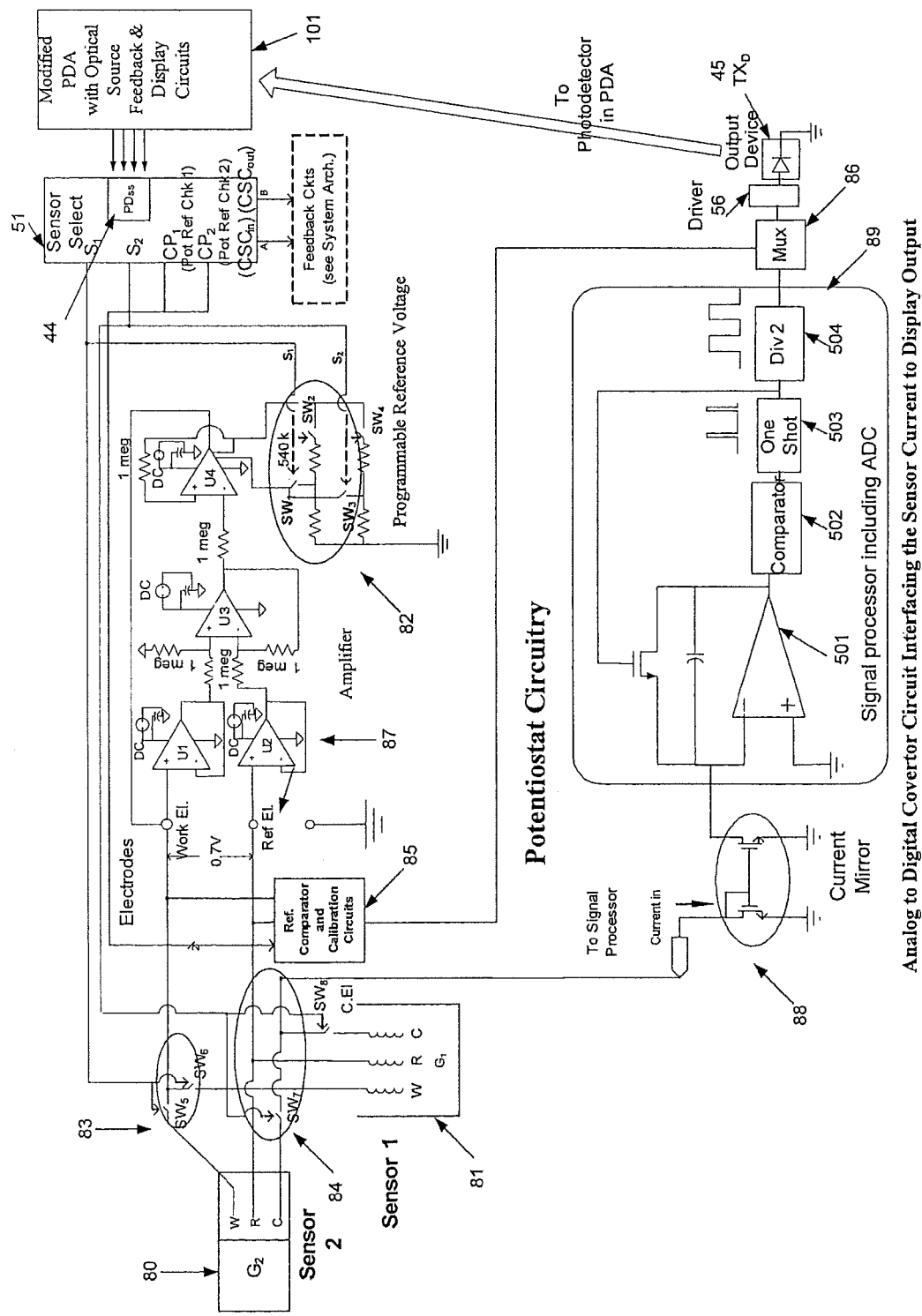
FIG. 5. Schematic of a programmable potentiostat interfacing with two sensors whose signal is processed by the signal-processing unit. The optoelectronic transmitter and receiver interface communicating with the implanted chip and the modified PDA is also shown.

FIG. 5 illustrates the selection of one sensor (80 or 81) from an implantable sensor platform that comprises more than one sensor (80, 81). It also demonstrates the operation of a programmable potentiostat consisting of operational amplifiers (87) and associated resistor network (82) assisting in the determination of the appropriate voltage between the Reference (R, shown in 80 or 81) and the Working (W, shown in 80, 81) electrodes of the selected sensor. A set of coded optical (850-980 nm) pulses (34) (see FIG. 2) transmitted by the $TX_{SS}$ (18), located in the modified-PDA unit (101) are received by the photodetector $PD_{SS}$ (44). The pulses enable selection of a function (such as potentiostat reference check, sensor selection, calibration or reading, or checking solar input power level etc.). These are enabled with the help of sensor select block 51, switches (shown as 82, 83, 84; and realized by transistors in integrated circuit chip), circuits lumped in block 85 and Mux 86. The outcome of this function is communicated back to the modified-PDA using the 1.55 μm optical pulse transmitter (45, located at bottom right corner). Using logic/router block 85 (consisting of reference comparator and calibration circuits), we can provide the information to MUX (Multiplexer) circuit (86), which in turn connects, to the driver (56) of $TX_D$. The use of different wavelengths and pulse frequencies for the two transceivers (one for sensor select and the other for rest of the functions) will further ensure minimal interference. Here, the sensors (80,81) interface with the current mirror 88, and signal processor 89, and Mux 86, and the driver 56, and the transmitter $TX_D$ (45). The current mirror (88) processes the sensor current and the ADC (89) converts into electrical pulses of different frequencies depending on the sensor-produced current level. The driver (56) makes it suitable to drive the output light emitting device (45, $TX_D$). In the case of ADC, we show an operational amplifier (501), a comparator (502), One shot (monostable multivibrator, 503), and a Divider by 2 circuit (Div 2, 504). There are many variations to implement this.

In one embodiment, two sensors (S1 and S2) are connected to a programmable potentiostat whose reference voltages will be selected on the sensor under test. The signal processing units can be miniaturized by reducing the design rules (fineness of microelectronic features) from 0.35 μm to 0.12 μm and below.

Figure 6:
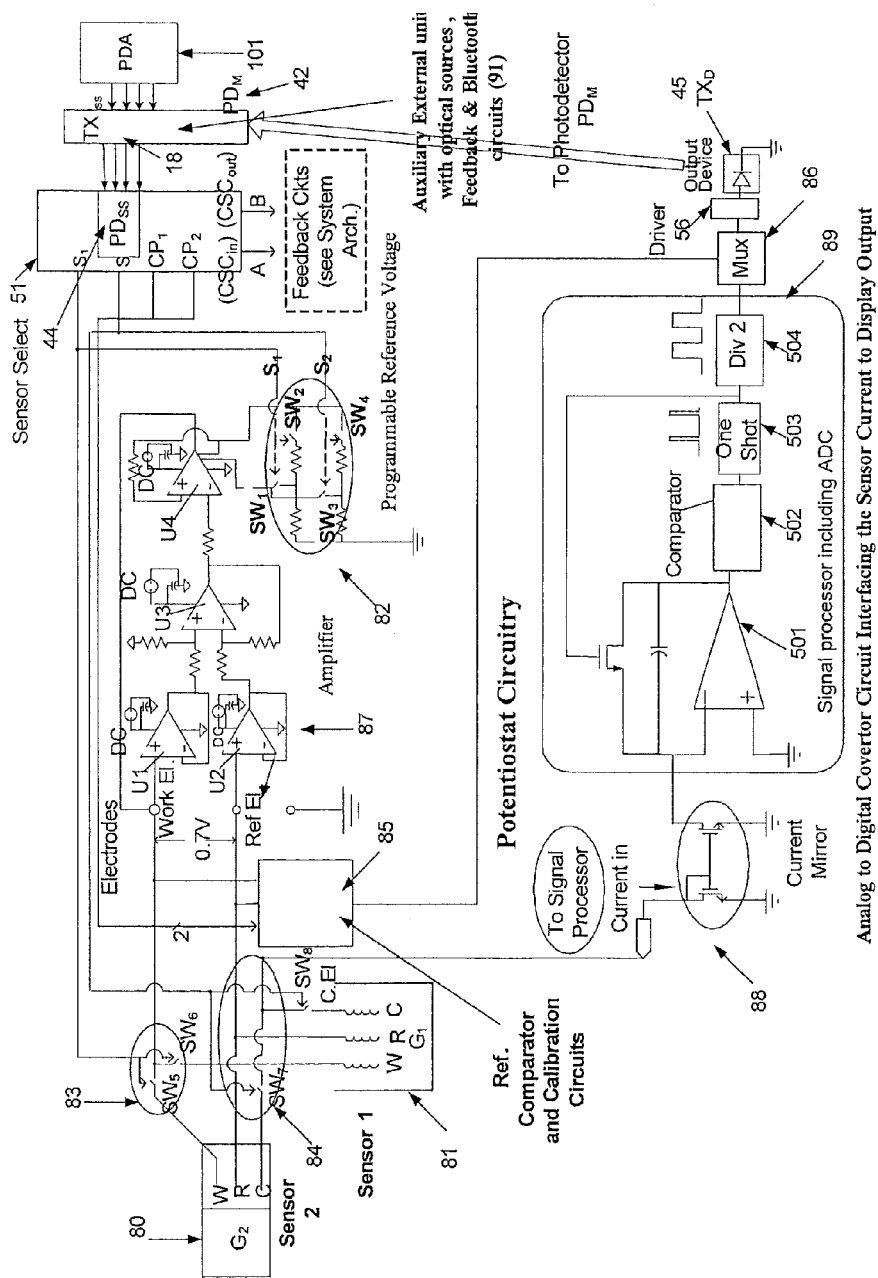
FIG. 6. Schematic of a PDA communicating wirelessly with an external unit that is located in the vicinity of the implantable platform.

In one embodiment, two sensors (S1 and S2) are connected to a programmable potentiostat whose reference voltages will be selected on the sensor under test. The control lines and associated switches (to be replaced by FETs) in the FIGS. 5 and 6 are used to perform select function (including sensor selection S1 or S2 (see FIG. 7)) or CP1 and CP2. The signal processing units can be miniaturized by reducing the design rules (fineness of microelectronic features) from 0.35 μm to 0.12 μm and below.

In one embodiment, the device is run in self-calibration mode. The potentiostat reference voltage [CP1 or CP2 (Potential Reference Check 1 or 2) by comparing the voltage difference between the reference and corresponding working electrode], power level and/or voltage out put of the solar cells that are powering the entire chip and transceivers can be checked when the device is in self-calibration mode. Built-in comparators and logic are used to achieve the self-calibration functions. In operation, a comparator receives a specific signal and compares it with the reference (voltage) and depending on the difference generates a decision, which is then executed via the logic circuits. For example, the circuit block labeled "Ref. Comparator and Calibration Circuits" (85) along with the multiplexer (Mux) (86) enable utilization of the 1.55 μm transmitter to report back to the PDA the desired information. (FIG. 5)

FIG. 6 shows an alternate scheme wherein a PDA unit is interfaced via wireless technology (e.g., Bluetooth®) to an auxiliary external unit (91), which communicates with the implanted sensor. The signal (from PDA or modified PDA (101)) is received by unit 91, this signal is converted into optical pulses by an optical transmitter $TX_{SS}$ (18). This signal is received by photodetector $PD_{SS}$ (44) in the implanted unit. The information from the implanted sensor is received by photodetector PDM (42) now located in the auxiliary external unit (91) which in turn transmits it back to the PDA (101). This type of arrangement is envisioned in circumstances where a PDA unit is not a dedicated unit for monitoring analytes.

Figure 7:
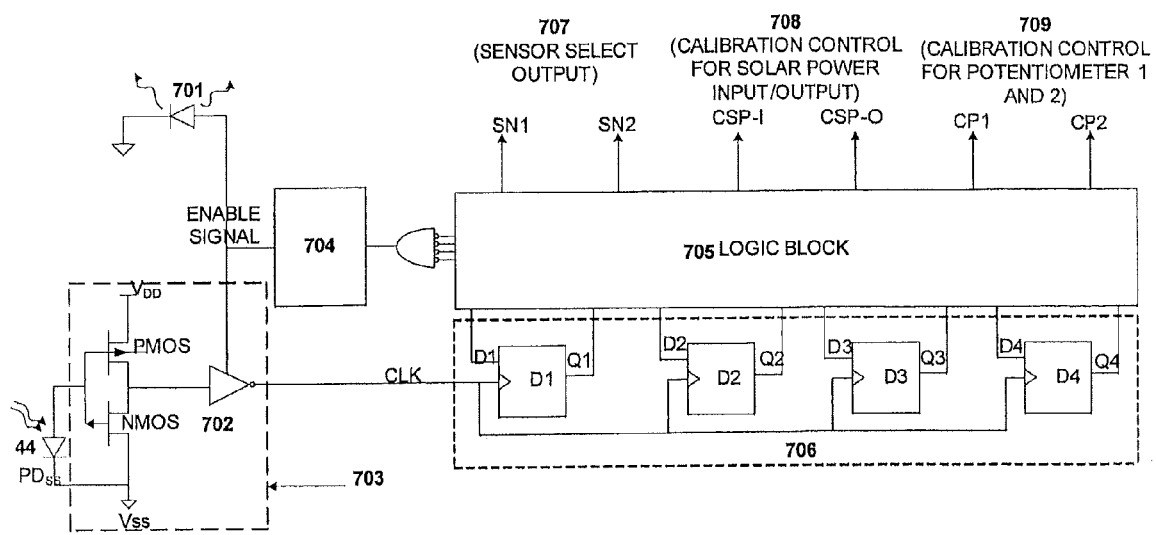
FIG. 7. Embodiment of a design of sensor-select circuit. This circuit consists of a optical pulse receiving system, a timer, set of D-Flip Flops, and a logic block. It interfaces calibration and Mux (multiplexer) circuits.

FIG. 7 shows an embodiment of a design of sensor select circuit. The circuit has a photodetector (shown as diode on the extreme left) $PD_{SS}$ (44). This photodetector receives optical pulses (800-950 nm) from the transmitter $TX_{SS}$ (18) located in the external unit (see FIG. 2). The signal is amplified by circuit shown in block (703) which consists of an inverting amplifier (two transistors) and a ti-state buffer (702). Block (704) is the timer that generates clock pulse based on our logic block (705) operation. Depending on the pulse code, one of the six outputs (labeled as 707, 708, and 709) gets activated. The activation depends on block (706, consisting of D-Flip Flops) and Logic Block (705). For example, if the pulse code is set for selection of Sensor#1 left most output SN1, shown as part of (707), is selected. This means a high voltage is available, which in turn will activate switches 82, 83, and 84 (see FIG. 5). This selection also activates the Router/Logic/Mux (FIG. 1, FIG. 5) circuit in a certain way to enable the activation of $TX_D$ (45) through driver (56). The transmitter $TX_D$, operating at 1.55 μm, sends a signal showing the selection of Sensor 1. Details of logic (705) and MUX (86 in FIG. 5) circuits are not shown here.

When Mode select (13, FIG. 1) sends a code for calibration check of potentiostat, CP1 and CP2 (shown as 709) are activated. Similarly, mode select (13) can select calibration control to check power level of solar cells (41) using CSP-I and CSP-0 (708). In FIG. 5, the solar power check is written as CSC (in block 51).

Circuit designers may implement this concept in a variety of ways.

Figure 8:
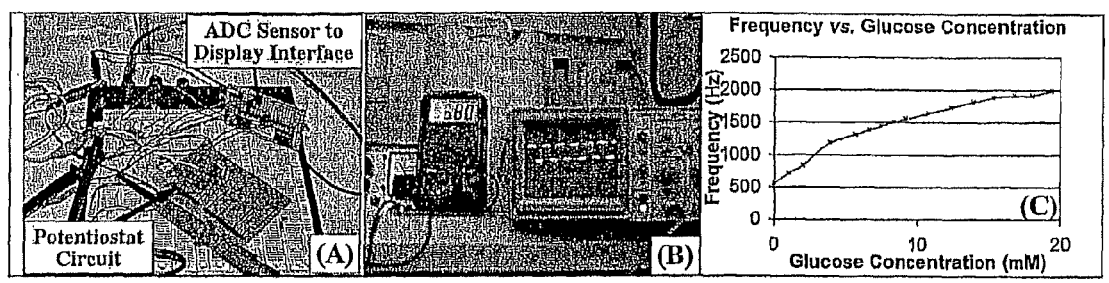
FIG. 8. Figure A showing an ADC signal processor (MOSIS fabricated chip) interfaced with a hybrid potentiostat. (B). Measurements showing digital signal changing its pulse characteristics as a function of glucose level. (C). Plot of glucose level after converting the pulse frequency change.

FIG. 8 shows photographs of an embodiment of a working glucose sensor and the data obtained therefrom. FIG. 8 (A) shows an ADC signal processor (MOSIS fabricated chip) interfaced with a hybrid potentiostat. FIG. 8(B) shows the digital pulses on an oscilloscope along with the potential difference (680 mV shown on a meter) between the working and reference electrode of a functional glucose sensor. The electrochemically detected glucose concentration is encoded in terms of digital pulse frequency by the chips in FIG. 8(A). FIG. 8(C) illustrates a plot of glucose concentration as a function of digital pulsed frequency, generated by the signal processing chips shown in FIG. 8(A).

FIG. 9 shows first and second generation microelectronic sensor component embodiments. The dashed-line square and circle indicate the first and second generation components, respectively. Selected components (1-5) are further magnified in panels (B-F) along with their actual dimensions. (B) shows a $1^{st}$ generation (MOSIS-fabricated) integrated circuit that contains an ADC signal processor unit and two RF antennas. (C) shows a planar electrochemical sensor with three electrodes (working (Pt), counter (Pt) and reference (Ag/AgCl, whitish-appearing, right-most electrode)). (D) shows an InGaAsP semiconductor laser stack (8 in number) emitting infra red (IR) radiation of 1.55 μm. The sensor platform may be equipped with one of these lasers. (E) shows an individual, Si-based solar cell device. Typically 5 or 6 panels may be connected in series to power up all components of the implantable sensor platform. (F) shows a second generation (MOSIS-fabricated) integrated circuit containing the potentiostat and ADC signal processors, without the RF antennas. Stacking of all components from the second generation will result in about a 0.3×5 mm implantable platform with provision for 0.1 mm thick biocompatible coating on each side. The overall 0.5×5 mm sensor can be implanted through a 16 gauge hypodermic needle.

Figure 10:
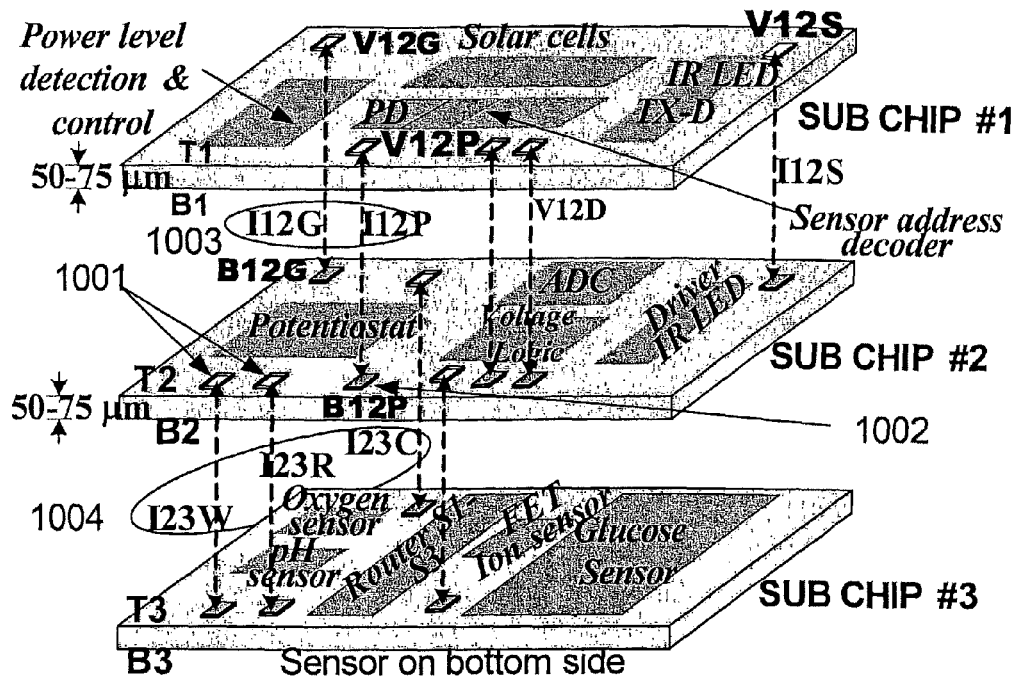
FIG. 10. (top) Hybrid approach to integrate sub-chips with robust interconnects and bonding using vias and bumps. (bottom left) Cross-sectional schematic illustration of bonding between a via and bump for sub-chip#1 and sub-chip#2. Top view of interconnect and power pad is also shown. (bottom right) Bonding between sub-chip#2 and sub-chip#3 is shown using two approaches for integration.
Figure 10:
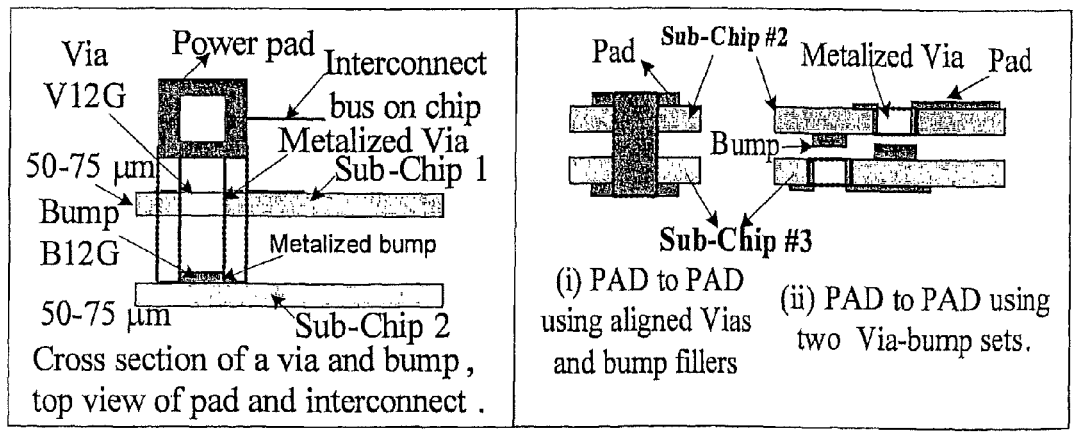

FIG. 10 shows an exemplary layout of three sub-chips using a hybrid approach to integrate sub-chips with robust interconnects 1003 between subchip#1 and subchip#2 (labeled as I12G for ground interconnect between subchip#1 and subchip#2, I12P for power or voltage supply) and interconnects 1004 between subchip#2 and subchip#3 (e.g. labels I23W, I23R and I23C; here W for working electrode, R for reference electrode and C for counter electrodes connections between sensors on subchip#3 and potentiostat on subchip#2). The subchips are connected using vias (1001) and bumps (1002). The vias are V12P, V12S, V12G (numeral 12 refer to subchips#1 and 2, and the letter P, S, and G refer to function such as power, signal and ground). The bumps 1002 shown on subchip#3 mate with the vias on the subchip above this (that is subchip#2). Bumps are designated as B12P (the bump on subchip#2 locks with the via on subchip#1; here P refers to power or voltage connection) and B12G (G for ground connection). Cross-sectional schematic illustration of bonding between a via and bump for sub-chips#1 and #2 (bottom left). Top view of interconnect and power pad are also shown. Bonding between sub-chip#2 and sub-chip#3 is shown using two approaches used in the integration (bottom right). In FIG. 2 the word 'vias' (301 and 302) was used for the complete connection between two subchips including via, interconnect and the bump.

Figure 11:
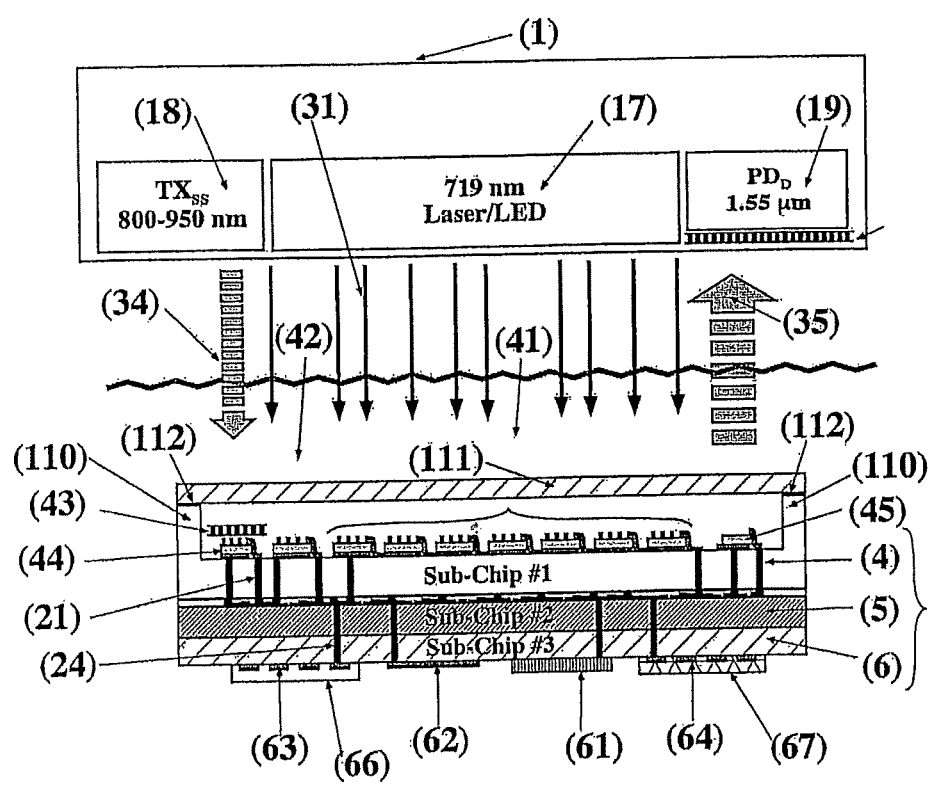
FIG. 11. Schematic of an embodiment of the three sub-chip design (shown in FIGS. 1, 2 and 3). Here the top surface of sub-chip#1 (4) is hermetically sealed using a transparent glass window (111) sealed to the raised silicon walls (110) via anodic bonding (112) between glass and silicon.

FIG. 11 shows another embodiment of a three sub-chip design (shown in FIGS. 1, 2 and 3) Here the top surface of Sub-chip#1 (4) is hermetically sealed using a transparent glass window (111) sealed to raised silicon walls (110) via anodic bonding (112) between the glass and the silicon. Similar hermetic seals are employed between the bottom surface of Sub-Chip#1 (4) and the top surface of Sub-Chip#2 (5), as well as the bottom surface of Sub-Chip#2 (5) and the back surface of Sub-Chip#3 (6). The front surface of Sub-Chip#3 (6) hosts various electrodes that are designed to operate in body fluids. All interconnects among sub-chips are vias filled with non-corrosive metals that provide hermetic seals for microelectronic and optoelectronic components of the implantable sensor platform.

Figure 12:
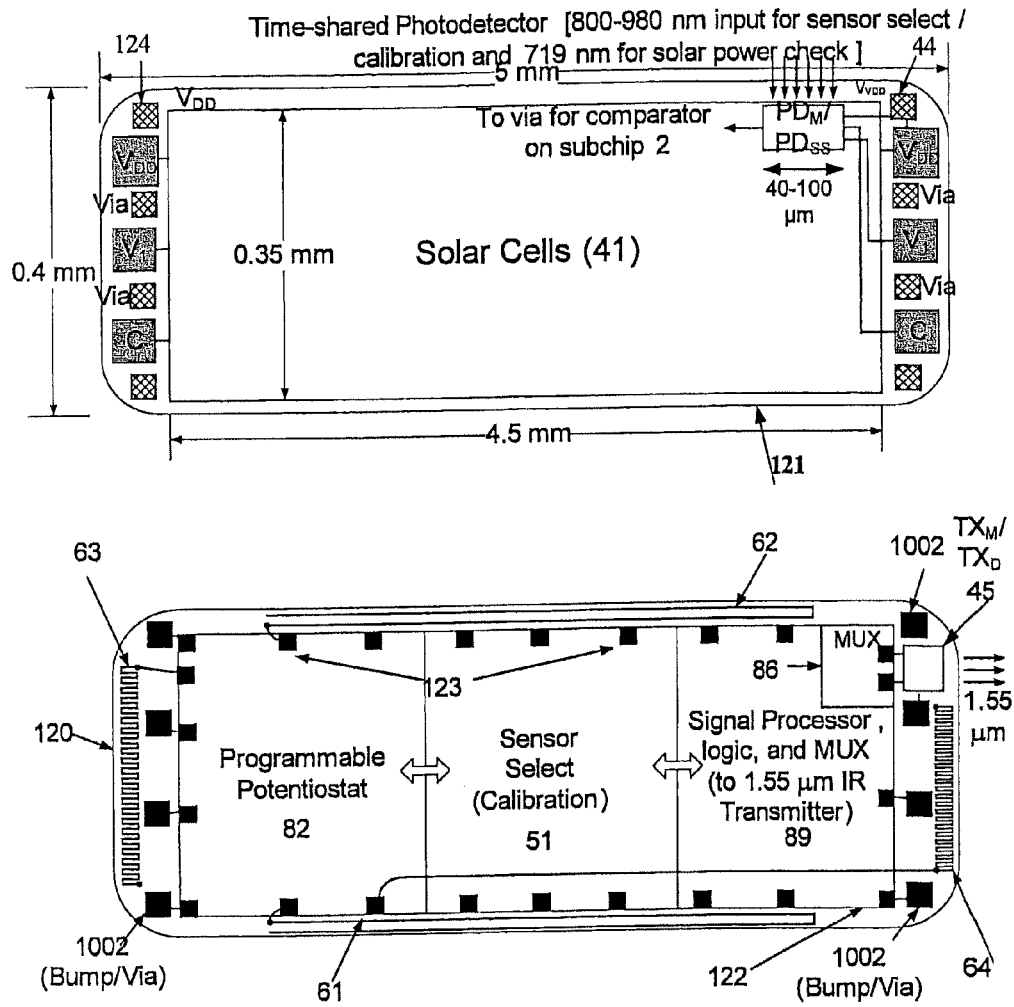
FIG. 12. Embodiment of a sensor platform having two sub-chips on its top and bottom surfaces. Sub-chip#1 has three pads on either side for power supply distribution (e.g., $V_{dd}$, $V_l$, and C for common, shown in blue and are larger in size than the via/bumps pads). The power is supplied to the sub-chip#2 using metalized vias labeled as $V_{VDD}$ etc. In addition, vias are used to connect photodetector $PD_{SS}/PD_M$ on sub-chip#1 to sub-chip#2 (having electronics such as sensor select, routing logic/MUX, etc.). Note that the 1.55 µm transmitter is located on sub-chip#2 as this wavelength is transparent to Si platform and chips.
Figure 12:
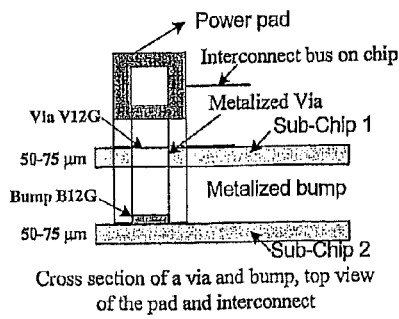

FIG. 12 shows an embodiment where the three sub-chip design has been implemented as two sub-chips. This design is possible using finer design rules (i.e., 0.35 micron versus 0.5 micron chip processing) for the potentiostat and signal processing components (usually located on sub-chip#2, FIG. 11), which results in saved space on a Si chip. As a result, functions of sub-chip#2 and sub-chip#3 could be integrated as one sub-chip (referred to as (120) the new-sub-chip#2); thus a sensor platform having two sub-chips can be realized. An exemplary embodiment is illustrated in FIG. 12. New-Sub-chip#2 (120), according to this embodiment, comprises a ~0.25×4 mm MOSIS chip (122) (like part 5 of FIG. 1, or electrical circuit of FIG. 5) bonded face down on the carrier 0.3×5 mm platform (120) that hosts along its perimeter the electrochemical sensor electrodes (61,62,63,64). The bonding pads (123) are connected to the bump and or vias (shown as 1002 and 124). Two working electrodes (63,64) are placed at either side along the width in a meander-form to improve adhesion of the glucose oxidase coating. Lengthwise, a Pt counter (62) and an Ag/AgCl reference electrode (61) are also placed to function in conjunction with either working electrode. In addition, a 1.55 μm InGaAsP transmitter $TX_D$ (45) (and $TX_M$ which is for monitoring and could be one unit via MUX (18) circuits) is placed on the upper right corner, adjacent to the working electrode 2 (64). The wafer carrier is a high resistivity (>20,000 Ohm/cm) Si (100) in which bumps, vias and interconnects are patterned and metallized prior to growing the organic layers for the electrochemical sensor. The bumps and vias are also shown. Both the MOSIS and the 1.55 μm InGaAsP transmitter chip are placed face down and their pads are connected to the pads on the carrier chip.

The subchip#1 (4) is shown as part new subchip#1 (121). In this embodiment, new-sub-chip#1 has 3 pads on either side for power supply distribution (e.g., $V_{dd}$, $V_1$ for voltages, and C for common). The power is supplied to the new-sub-chip#2 using metalized vias labeled as $V_{VDD}$ (124). In addition, vias are used to connect photodetectors $PD_{SS}$ (44) and $PD_M$ on new-sub-chip#1 to new-sub-chip#2 (having electronics such as sensor select, routing logic/MUX, etc.). Note that the 1.55 μm transmitter is located on new-sub-chip#2 as this wavelength is transparent to Si platform and chips. Solar cells (41) are not shown individually as in FIG. 2.

FIG. 13 shows embodiments of various circuits that may be integrated into two sub-chips: (subchip#1 (121 of FIG. 12 or 4 of FIG. 1) and subchip#2 (120) of FIG. 12. It also shows some circuits (14 called Add-on Devices & Control Circuits in FIG. 1) that may be housed in the modified PDA unit (101). Here, the modified PDA is communicating directly with the implanted unit.

Figure 14:
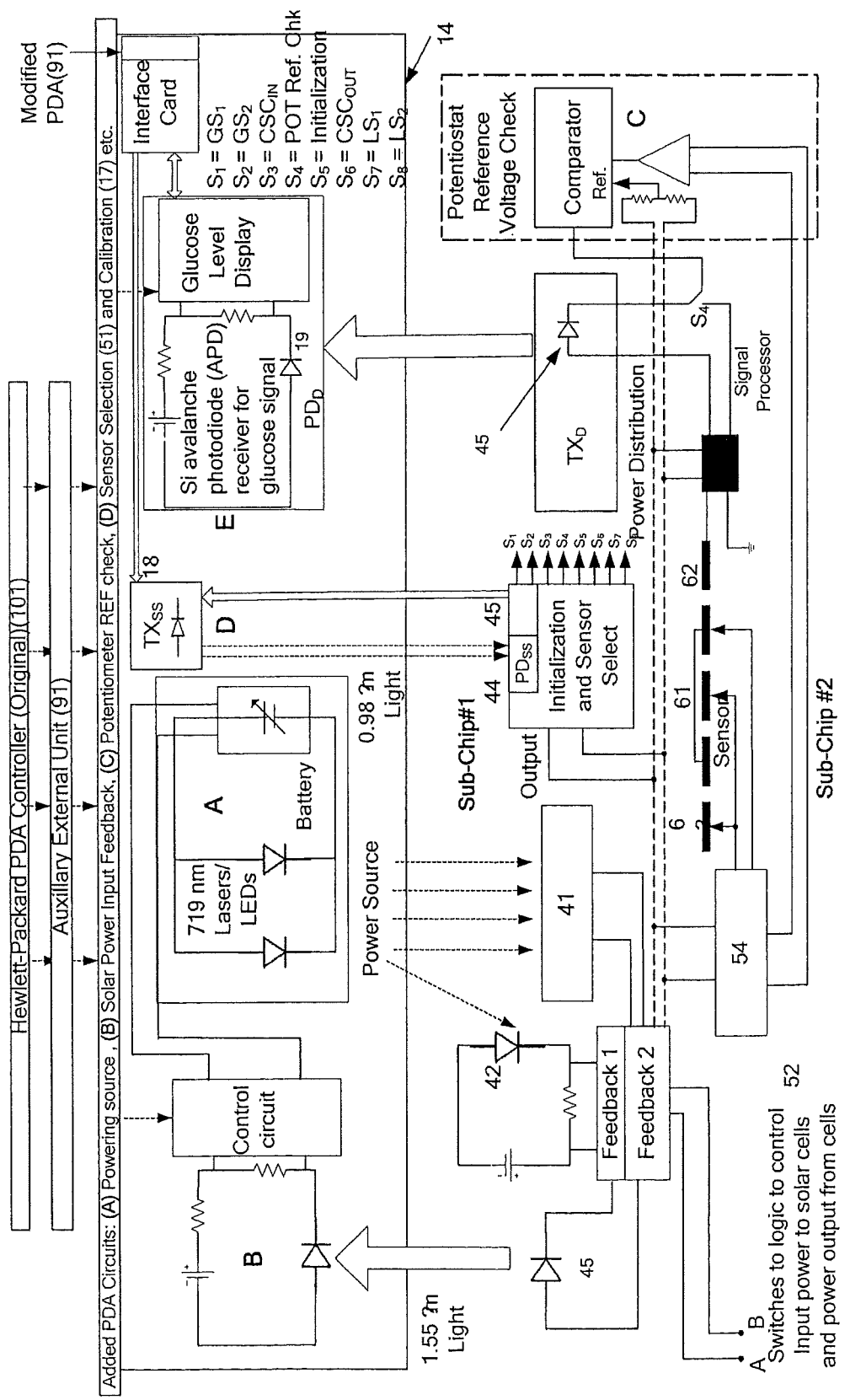
FIG. 14. Circuit schematic showing various functions of three sub-chips condensed into two sub-chips. In this version, the modified PDA unit communicates with an external unit located in the vicinity of the implanted sensor and the communication is via Bluetooth® wireless technology.

In some embodiments, it is advantageous to employ an auxiliary external unit (91) [of FIG. 6] that communicates with a PDA (101) on one hand and the implanted sensor platform on the other. This is shown in FIG. 14. In this embodiment, the PDA unit is communicating with an auxiliary external unit (91) via wireless technology (e.g., Bluetooth®). The external unit communicates with the implanted unit using optical communication.

Figure 15:
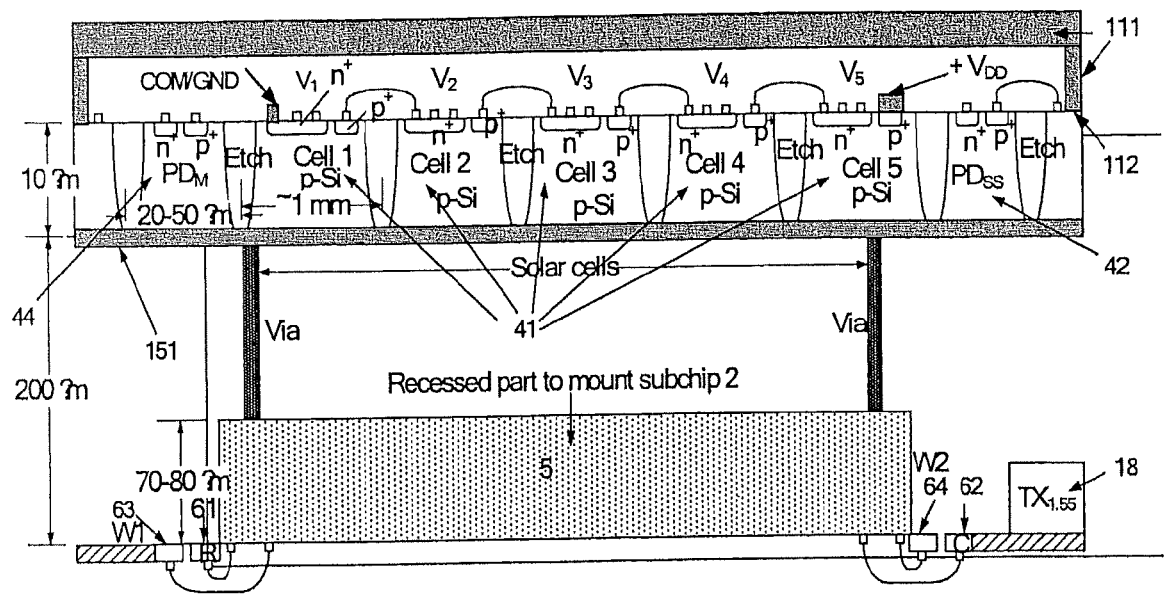
FIG. 15. Advanced methodology to integrate two sub-chips into one-wafer platform using wafer bonding technique. The hermetical seal using glass-Si anodic bonding is also shown for the solar cell/PDs chip.

FIG. 15 shows a methodology to integrate two sub-chips into one wafer platform using wafer bonding methodology. This advanced integration does not require vias and bumps as discussed above. In this embodiment, the photodetectors [$PD_M$ (44) and $PD_{SS}$ (42)] and solar cells (41) are realized on top part of the Si chip (~20-40 microns in thickness) having electrical resistivity in the 1-10 Ohm-cm. This wafer is bonded [using silicon dioxide layer (151) or other wafer fusion techniques known in the literature] to a high resistivity (~10,000 Ohm-cm) wafer. This wafer or the bottom side has sensors [comprising of various electrodes (61), (62), (63), and (64)] processed along with signal processing chip (5), which is mounted in a recessed part. The recessed part is created by deep RIE (reactive ion etching) or other technique. The top part of the wafer can be hermetically sealed using anodic bonding using glass 111 and bonded seals 112.

Figure 16:
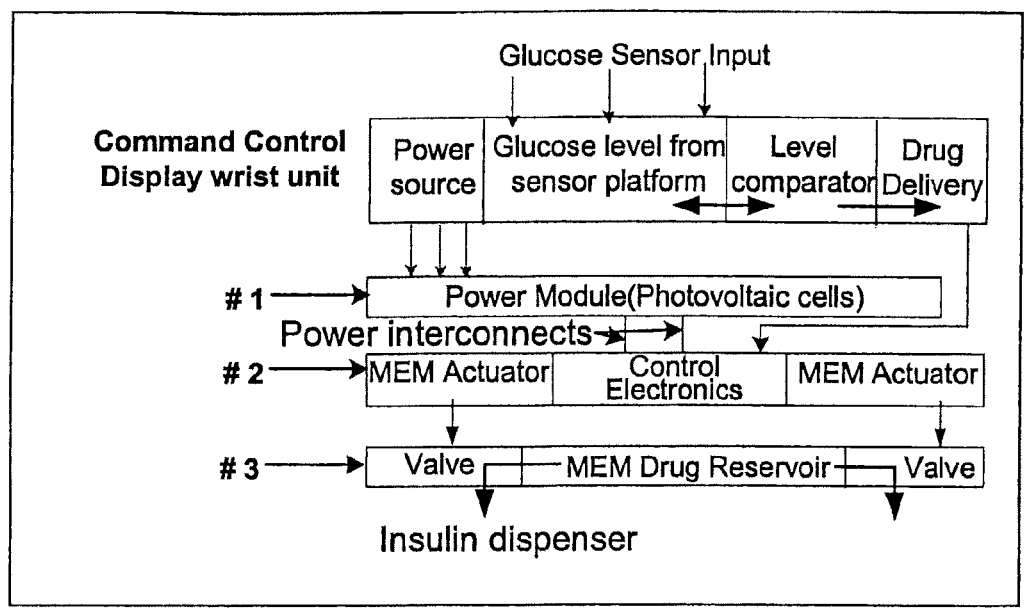
FIG. 16. Schematic of implantable sensor platform interfacing with a drug dispensing system. The drug delivery may include a micro-electro-mechanical (MEM) components.

FIG. 16 shows a methodology where the internal unit implantable platform (160) is integrated with drug delivery devices (shown as three modules below the command Control Display Wrist Unit (101D)). These units are also implanted separately or integrated along with the internal unit. Based on the implanted sensor reading of glucose or insulin, the control unit 101D (e.g. modified PDA unit) sends the signal to the insulin dispenser to dispense desired amount of insulin. Here, we have three sub-units or sub-modules identified as subchip#1 (powering module similar to part 4 of FIG. 1), Dispenser subchip#2 (161), and Dispenser subchip#3 (162). Subchip#1 provides the power to unit (161) and unit (162). Dispenser subchip (161) consists of sensor, signal processing [as carried out by subchip#2 (5) and subchip#3 (6) in FIG. 1], and control circuits (163) to actuate MEM (microelectrochemical) actuators (164, 165). MEM actuators activate Valves (166, 167) located on the Dispenser subchip #3 (162) which connect to the insulin drug reservoir (168). The insulin is dispensed via 173 and 174 if needed at two locations. The implanted biosensor in turn provides information regarding the glucose levels (169) or insulin levels. This information is fed to the processor (170) of the command unit (101D) where it is compared with expected insulin levels per software protocol and executed by Level Comparator unit (171). This in turn activates Drug Delivery Module (172) which relays the information to control electronic circuits (163).

The command unit (101D) has optical power source (17) for the solar cells (41) on subchip#1 (4).

Figure 17:
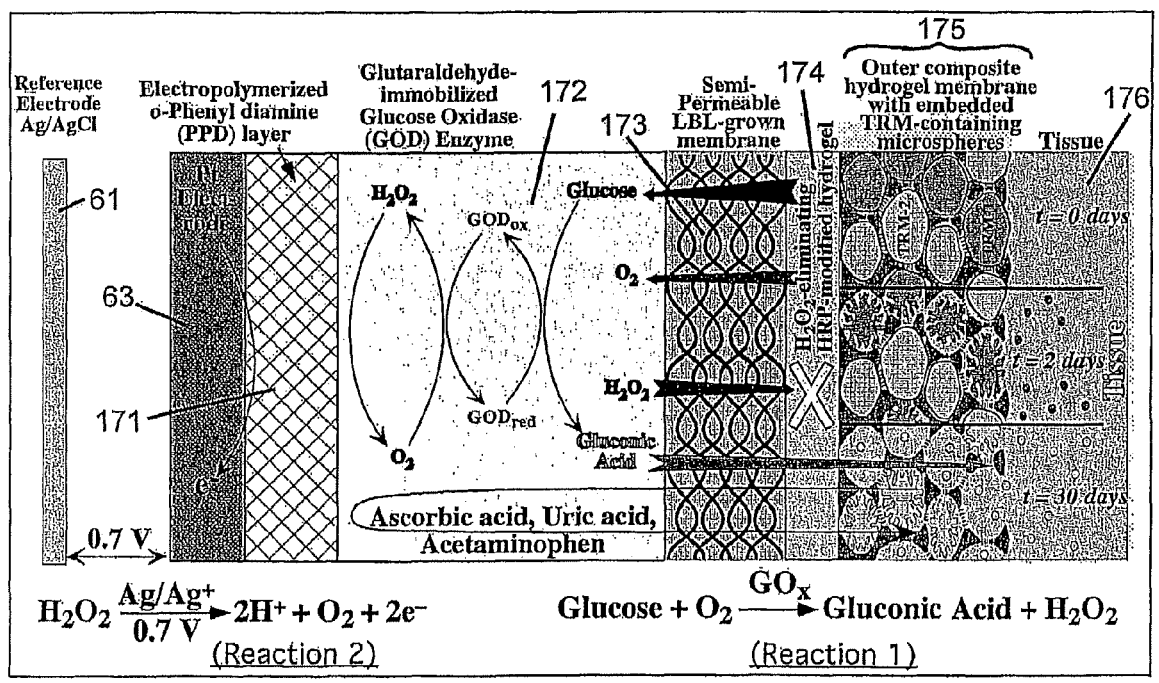
FIG. 17. Glucose sensor showing Ag reference electrode and details of coatings on Pt working electrode. Schematic representation of modified Clark amperometric glucose sensor, along with various chemical, electrochemical and diffusion processes associated with its operation. The glucose oxidase ($GO_x$) layer is coated with a semipermeable membrane to reduce the amount of glucose entering the sensor. An HRP-modified hydrogel layer is then applied to eliminate outer diffusion of $H_2O_2$. This is followed by an outer composite hydrogel coating with embedded microspheres at different stages of degradation and TRM release.

FIG. 17 illustrates glucose sensor with an Ag reference electrode and details of coatings on Pt working electrode. This is a schematic representation of modified Clark amperometric glucose sensor, along with various chemical, electrochemical and diffusion processes associated with its operation. The working Pt electrode (63 or 64 if more than one) is coated with electropolymerized o-phenylddiamine. PPD layer (171) (e.g., prevents permeation of ascorbic acid, acetaminophen etc.) is coated with glucose oxidase ($GO_x$) layer (172), which in turn is coated with a semipermeable humic acid membrane (173) to reduce the amount of glucose entering the sensor. An HRP-modified hydrogel layer (174) is then applied to eliminate the outer diffusion of $H_2O_2$. This is followed by an outer composite hydrogel coating with embedded microspheres at different stages of degradation and TRM release (175). The tissue is represented by (176).

In one embodiment, an enzyme-based glucose sensor operates on the principle of detection of hydrogen peroxide ($H_2O_2$) formed by glucose oxidation. Glucose oxidase ($GO_x$) acts as a catalyst, which turns glucose into gluconic acid (Reaction 1) and produces $H_2O_2$. $H_2O_2$ is electrochemically oxidized (Reaction 2) under an applied potential of 0.7 V and the current measured is related to the glucose concentration (see diagram in FIG. 17). The semipermeable membrane, depicted in FIG. 17, in addition to assisting in prevention of biofouling, is designed to regulate glucose diffusion. It is well known that for an enzyme-based implantable sensor to work at its optimum efficiency in tissue, the ratio of oxygen, which regenerates the enzyme, to the permeating glucose should remain constant. Typically, the physiological levels for glucose and oxygen in subcutaneous tissue are 5.6 and 0.1 mM, respectively. Thus, in the absence of a diffusion-limiting barrier for glucose, the kinetics of $H_2O_2$ production may be oxygen-limited due to the significantly larger amount of glucose compared to oxygen. At high glucose concentrations, this oxygen limit can lead to reduced glucose sensitivity. Therefore, a method to achieve accurate monitoring of glucose over the entire physiological concentration range with high sensitivity and short response time an outer membrane with tunable permeability properties is needed. Such a membrane has been developed through layer-by-layer grown polyelectrolytes and/or multi-valent cations.

The GOx and/or carrier protein concentration may vary. For example, the GOx concentration is about 50 mg/ml (approximately 10,000 U/ml) to about 700 mg/ml (about 150,000 U/ml). In particular, the GOx concentration is about 115 mg/ml (approximately 22,000 U/ml). In such embodiments, the HSA concentration is about 0.5%-30% (w/v), depending on the GOx concentration. In particular, the HSA concentration is about 1-10% w/v, and most particularly is about 5% w/v. In alternative embodiments, collagen or BSA (Bovine Serum Albumin) or other structural proteins used in these contexts can be used instead of or in addition to HSA. Although GOx is discussed as an enzyme in the sensor element, other proteins and/or enzymes may also be used or may be used in place of GOx, including, but not limited to glucose dehydrogenase or hexokinase, hexose oxidase, lactate oxidase, and the like. Other proteins and/or enzymes may also be used, as will be evident to those skilled in the art. Moreover, although HSA is employed in the example embodiment, other structural proteins, such as BSA, collagens or the like, can be used instead of or in addition to HSA.

For embodiments employing enzymes other than GOx, concentrations other than those discussed herein may be utilized. The concentration may be varied not only depending on the particular enzyme being employed, but also depending on the desired properties of the resulting protein matrix. For example, a certain concentration may be utilized if the protein matrix is to be used in a diagnostic capacity while a different concentration may be utilized if certain structural properties are desired. Those skilled in the art will understand that the concentration utilized may be varied through routine experimentation to determine which concentration (and of which enzyme or protein) may yield the desired result.

Figure 18:
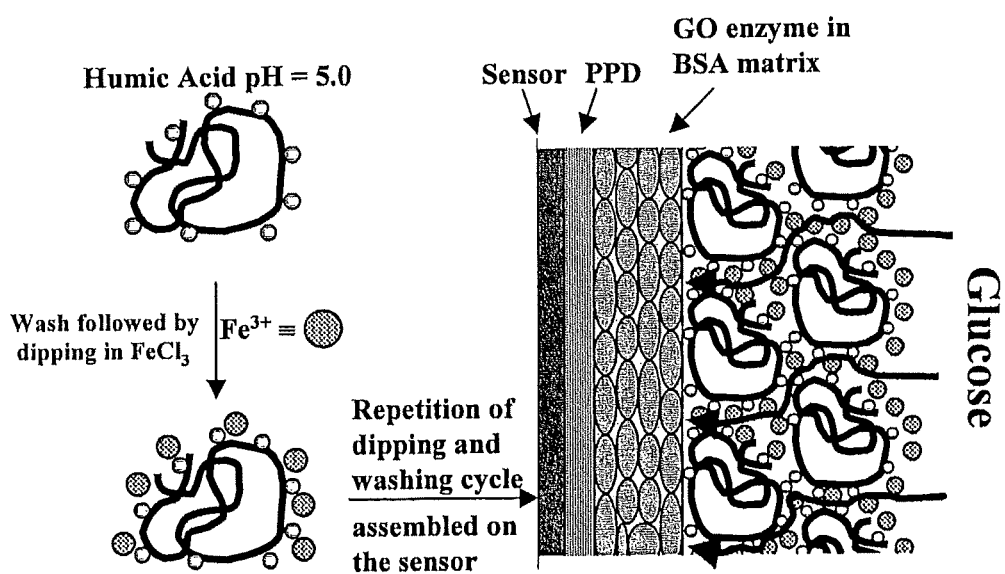
FIG. 18. Schematic of the self assembly of semipermeable membrane composed of humic acids and $Fe^{3+}$ on the outer surface of the electrochemical sensor. As the number of bilayers increases, there is an increase in the tortuosity for glucose diffusion towards the enzyme.

FIG. 18 shows the self-assembly of semipermeable membrane composed of humic acids and $Fe^{3+}$ on the outer surface of the electrochemical sensor. As the number of bilayers increases, there is an increase in the tortuosity for glucose diffusion towards the enzyme. The glucose oxidase ($GO_x$)

layer is coated with a semipermeable humic acid membrane to reduce the amount of glucose entering the sensor.

For testing purposes, a miniaturized sensor (shown in FIG. 9) made of platinum evaporated on a high resistivity Si wafer has been developed. To ensure Pt bonding to the Si wafer, a number of coatings have been employed to eliminate delamination problems once implantation takes place. In particular, Au/Ti/Pt/Ti/Ag coatings may be employed. Silver is removed from the working and counter electrodes. Ag is converted to AgCl to form a reference electrode. In the case of the working electrode, a film of poly (o-phenylenediamine) is electropolymerized on the working electrode, following which the sensing enzyme, i.e., glucose oxidase, is immobilized on top. Finally a semipermeable membrane composed of humic acids and $Fe^{3+}$ ions is grown on the device through electrostatic self-assembly. The sensor is tested via amperometry in phosphate buffered saline (PBS) solution maintained at 37° C. Glucose is added to the solution following which a pulse of 0.7V is applied to the device every 5-10 minutes until a constant current reading is obtained. Once the device has stabilized, glucose concentration is incremented and the process repeated to generate a calibration curve as shown in FIG. 16.

Figure 19:
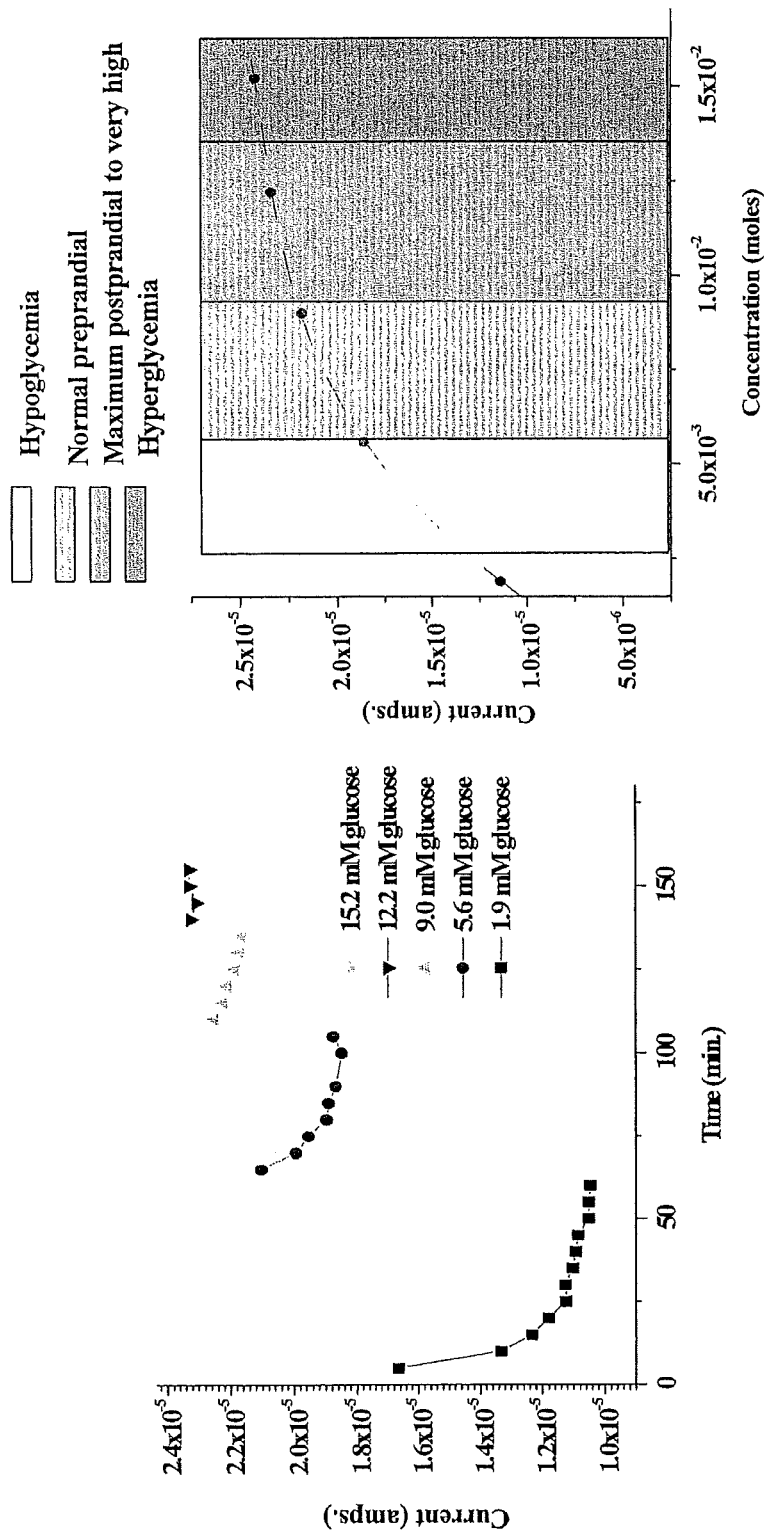
FIG. 19. One-second pulsed mode operation of sensor. Calibration curve of current response vs. change in glucose concentration. As the amount of glucose in the system is increased, there is a corresponding rise in the current. The Figure on left indicates the time required for the device to stabilize at each glucose concentration. As the concentration of glucose increases, the device reaches a stable reading faster.

FIG. 19 illustrates pulsed mode operation of the sensor. In pulsed mode operation, voltages are applied to various sensor electrodes for a certain duration. Calibration curve of current response vs. change in glucose concentration is shown for different glucose concentrations. As the amount of glucose in the system is increased, there is a corresponding rise in the current. The Figure on left indicates the time required for the device to stabilize at each glucose concentration. As the concentration of glucose increases, the device reaches a stable reading faster.

Figure 20:
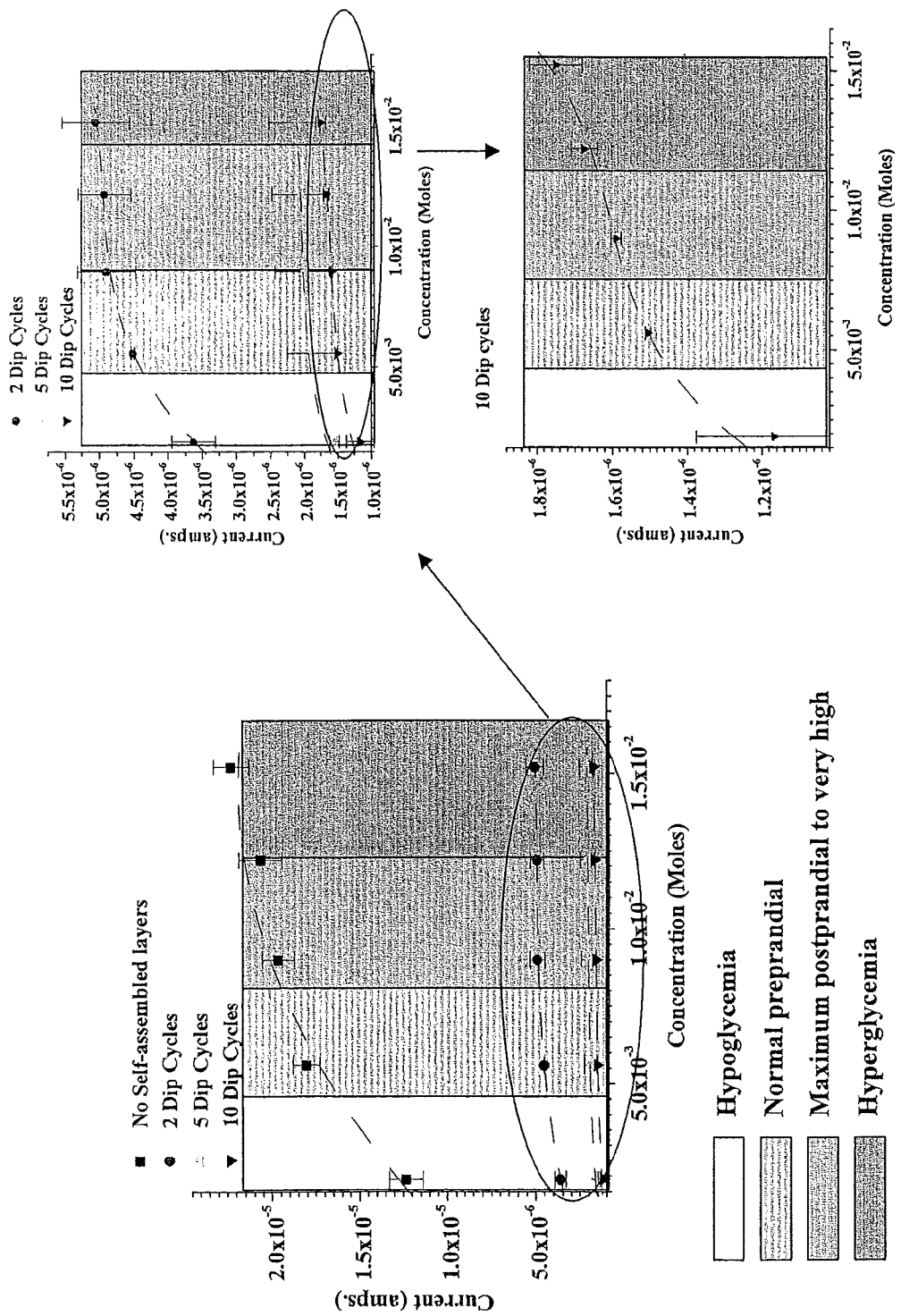
FIG. 20. Current response as a function of increasing semipermeable membrane thickness.

FIG. 20 shows that by varying the number of dip-cycles (2, 5 and 10), the current is reduced by almost 10 fold, while maintaining current linearity. The thickness of the film depends on the number of dip-cycles. The ability of these membranes to act as an efficient barrier for glucose permeation has thus been demonstrated.

Figure 21:
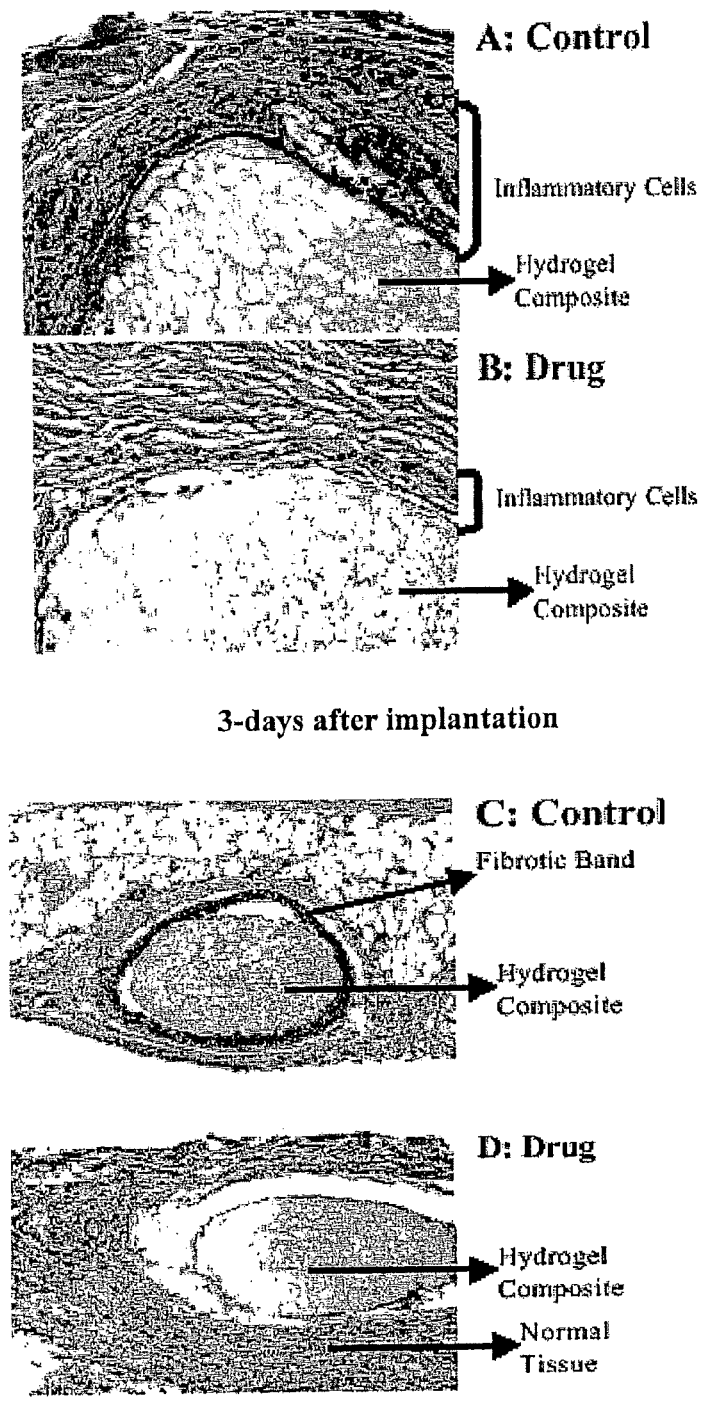
FIG. 21. Histological evaluation of subcutaneous tissue samples taken from the vicinity of hydrogel composites containing PLGA microspheres at 3 and 21 days post implantation. The representative sections shown are 3 days after implantation (A & B) and 21 days after implantation (C & D).

FIG. 21 shows histological evaluations of subcutaneous tissue samples taken from the vicinity of hydrogel composites containing PLGA microspheres at 3 and 21 days post implantation. The representative sections shown are 3 days after implantation (A & B) and 21 days after implantation (C & D). There seems to be no inflammation showing the effectiveness of the coatings.

Figure 22:
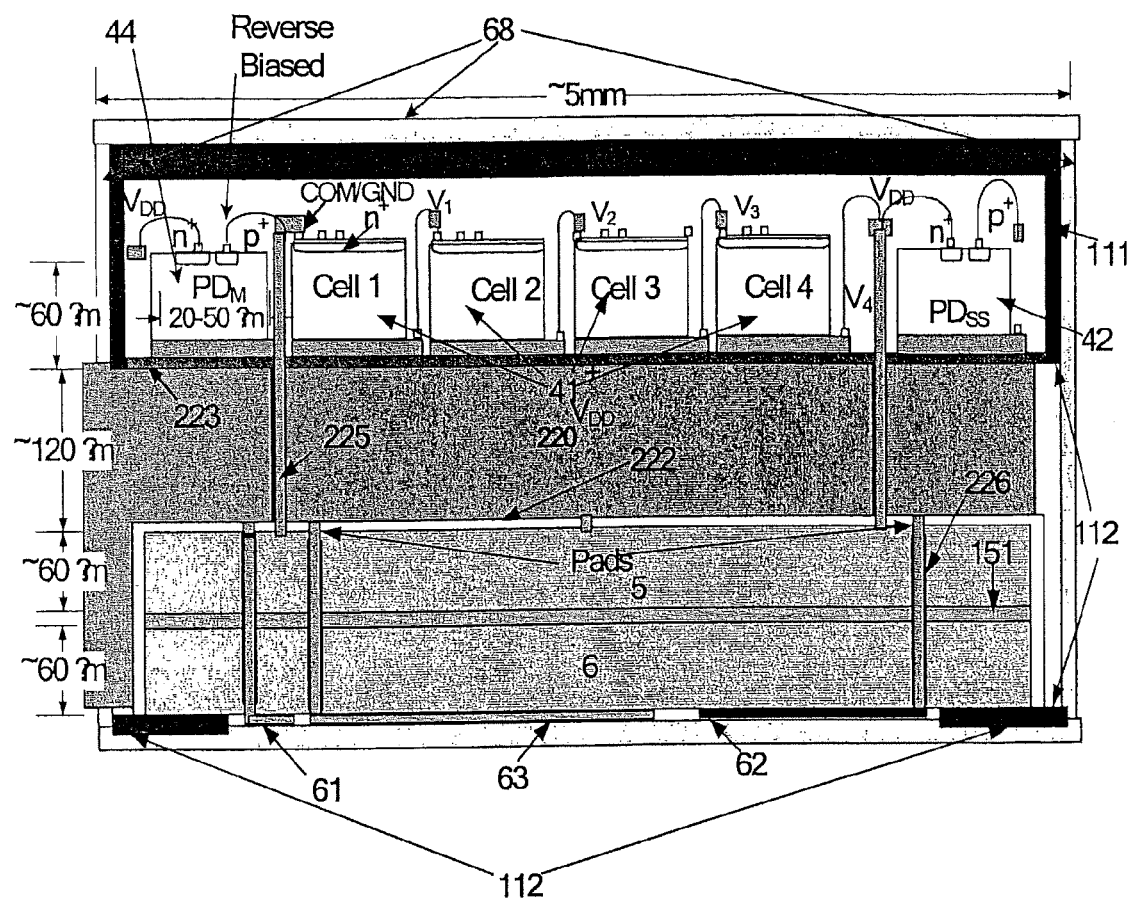
FIG. 22. schematic of a methodology to hermetically seal sub-chips using one Si wafer as the carrier with provision to placing sub-chips and interconnecting them. The hermetical seal using glass-Si anodic bonding is shown on top as well as bottom.

FIG. 22 shows a schematic cross-section of an embodiment of implantable sensor platform with a methodology to hermetically seal sub-chips using one high resistivity Si wafer as the carrier (220) which has one recessed region (221) on one side. In this region solar cells (41) are bonded on metallic pads (224) deposited on an oxide layer (223). Photodetectors (44) and (42) are also placed on this side. The carrier wafer (220) body is recessed (222) on the other side as well. Thinned sub-chips 2 (5) and subchip#3 (6) are placed in the recessed region (222).

The sub-chips can be electrically interconnected using interconnects like (226) which run in vias like (225) as shown or other standard interconnect techniques may be used. The hermetical seal provided by the glass-Si anodic bonding (112) is shown on top as well as bottom surfaces of the carrier (220). This is an alternate approach for three sub-chip integration as shown in FIGS. 11 and 15.

A variety of optional items may be included in the sensor platform. One optional item is a temperature probe. One exemplary temperature probe comprises two probe leads connected to each other through a temperature-dependent element that is formed using a material with a temperature-dependent characteristic. An example of a suitable temperature-dependent characteristic is the resistance of the temperature-dependent element. The two probe leads comprise, for example, a metal, an alloy, a semimetal, such as graphite, a degenerate or highly doped semiconductor, or a small-band gap semiconductor. Examples of suitable materials include gold, silver, ruthenium oxide, titanium nitride, titanium dioxide, indium doped tin oxide, tin doped indium oxide, or graphite. The temperature-dependent element can further comprise a fine trace (e.g., a conductive trace that has a smaller cross-section than that of the probe leads) of the same conductive material as the probe leads, or another material such as a carbon ink, a carbon fiber, or platinum, which has a temperature-dependent characteristic, such as resistance, that provides a temperature-dependent signal when a voltage source is attached to the two probe leads of the temperature probe. The temperature-dependent characteristic of the temperature-dependent element can either increase or decrease with temperature.

The sensor platform comprises components manufactured from biocompatible materials, such as materials that are corrosion resistant, INCLUDING Pt, $SiO_2$ coatings, and glass thin films. In addition, corrosion resistant materials that are harmless to tissues in biologic environments, such as silicon and heavily boron-doped silicon can be used in the manufacture of the components of the internal unit. Another method by which the corrosion resistance of the internal unit can be improved is through coating of the internal unit with titanium, iridium, Parylene (a biocompatible polymer), or various other common and/or proprietary thick and thin films.

The sensor platform optionally comprises a biocompatible coating. The bioactive polymers are generally biocompatible, that is, physiologically tolerated, and do not cause substantial adverse local or systemic responses. While synthetic polymers such as poly(tetrafluoroethylene), silicones, poly(acrylate), poly(methacrylate), hydrogels, and derivatives thereof are most commonly used, natural polymers such as proteins and carbohydrates are also suitable. The bioactive polymer layer functions to protect the implant, preserve its function, minimize protein adsorption onto the implant, and serve as a site for the delivery of the tissue response modifying agents and drugs as well as other drugs and factors.

In one embodiment, the bioactive polymer layer comprises a hydrogel. Hydrogels are formed from the polymerization of hydrophilic and hydrophobic monomers to form gels and are described, for example, in U.S. Pat. No. 4,983,181 and No. 4,994,081, which are incorporated by reference herein. Hydrogels consist largely of water, and may be crosslinked by either chemical or physical methods. Chemical crosslinking is exemplified by the free-radical induced crosslinking of dienes such as ethylene glycol dimethacrylate (EGDMA), and the like. Physical crosslinks are formed by copolymerizing a hydrophobic co-monomer with the water-soluble monomer, and then by contacting the copolymerized gel with water. Physical association of the hydrophobic regions of the gel results in the formation of physical crosslinks. Control of the ratio of hydrophilic to hydrophobic monomers allows control of the final properties of the gel. Physical crosslinks can also be formed by freeze/thaw methods, for example freeze/thawing a poly(vinyl alcohol) (PVA) hydrogel. Highly water-swollen hydrogels are bioactive, and have minimal impact on the diffusion rates of small molecules. Hydrogels are also intrinsically mobile, and therefore have minimal deleterious effects on associated peptide tissue response modifiers.

Hydrogels may be formed by the polymerization of monomers such as 2-hydroxyethyl methacrylate, 2-hydroxyethyl methacrylate, fluorinated acrylates, acrylic acid, and methacrylic acid, and combinations thereof. Suitable hydrogels include copolymers of 2-hydroxyethyl methacrylate, wherein the co-monomers are selected to improve mechanical strength, stability to hydrolysis, or other mechanical or chemical characteristics. Copolymerization with various acidic monomers can decrease the buffer capacity of the gel, and thus modulate the release of the tissue response modifier. Suitable co-monomers include, but are not limited to, 3-hydroxypropyl methacrylate, N-vinyl pyrrolidinone, 2-hydroxyethyl acrylate, glycerol methacrylate, n-isopropyl acrylamide, N,N-dimethylacrylamide, glycidyl methacrylate, and combinations thereof. Suitable hydrogels are terpolymers of 2-hydroxyethyl methacrylate (HEMA), N-vinyl pyrrolidinone (NVP), and 2-N-ethylperfluorooctanesulfanamido ethyl acrylate (FOSA) with added EGDMA to provide controlled crosslinking. HEMA is hydrophilic, and swells in the presence of water. The hydroxyl groups of HEMA also provide potential sites for the covalent attachment of tissue response modifiers, slow release delivery systems, and the like. Acrylic acid, methacrylic acid, and other functionalized vinyl monomers can also be employed to provide these attachment sites. NVP is amphiphilic, wherein the backbone ring provides hydrophobicity and the polar amide group provides hydrophilicity. Poly(vinyl pyrrolidinone) is water soluble, physiologically inactive, and forms complexes with a number of small molecules such as iodine and chlorhexidine. Use of NVP improves the toughness of polymerized HEMA, and provides for the enhanced solubility of the other monomers under bulk polymerization conditions.

An example of a bioactive layer generated by self-assembly is the formation of NAFION™/$Fe^{3+}$ multilayer films. NAFION™ is a perfluorinated electrolyte having sulfonic acid functionalities that has been previously used as a semi-permeable membrane for electrochemical sensors. However, the strong ion-exchange properties of NAFION™ lead to calcification in vitro and in vivo. The sulfonate ($R-SO_3$) groups present in the hydrophilic domains of the membrane act as nucleating sites for deposition of calcium phosphate. These crystals tend to inhibit metabolite transport through the membrane, and also cause the membrane to become brittle and eventually crack. Electrostatic assembly of NAFION™ and $Fe^{3+}$ from dilute solutions of ferric citrate at a pH about 2 to 6 can be used to prevent calcium deposition.

A natural bioactive coating is a mussel adhesive protein (MAP). Self-assembly of biological materials such as mussel adhesive proteins allows the incorporation of materials, which improve implant biocompatibility. MAP produced by the blue seal mussel (*Mytilus edulis*) generally comprises 75 to 85 repeating decameric units having the primary sequence of KPSY-Hyp-Hyp-T-DOPA, wherein Hyp is hydroxyproline and DOPA is 3,4-dihydroxyphenylalanine. DOPA is a strong metal chelating agent, particularly with $Ca^{2+}$ and $Fe^{3+}$, and the strong self-aggregation of DOPA in the presence of cations results in supra-molecular self-assembly. Accordingly, a substrate comprising metal chelating groups, for example free amine groups, is sequentially immersed first in a solution comprising metal ions (i.e., $Ca^{2+}$ and/or $Fe^{3+}$) (followed by optional washing in fresh solvent); and second, in a solution comprising the poly(ligand) (i.e., the MAP protein) (followed by optional washing in fresh solvent). The thickness of the membrane will be directly proportional to the number of sequential immersion cycles. The assembly of the membrane may be monitored with Variable Angle Spectroscopic Ellipsometry (VASE), UV-VIS and Quartz Crystal Microbalance.

The strong chelation between $Ca^{2+}$ and DOPA in the MAP membrane results in a substantial decrease in porosity, allowing the permeation of small molecules such as glucose and oxygen, while excluding permeation of larger molecules. Additionally, the introduction of small amount of crosslinking, via the Michael addition from neighboring lysine repeats by slight increase of pH above 8.5, which may be used to further fine-tune the permeability of such assemblies to levels.

Humic acids may also be polymerized, or self-assembled into a biocompatible layer. Humic acids or "humic substances" are heterogeneous, high-molecular weight organic acids having a large proportion of DOPA, and are resistant to microbial degradation. The known ability of humic acids to donate and accept electrons from a variety of metals and organic molecules explains their capability to shuttle electrons between the humic-reducing microorganisms and the Fe(III)-Fe(II) oxide. It has been suggested that humic acids participate in a biological electron transfer as a result of the electron accepting ability of quinone moieties when reduced to hydroquinones and vice-versa. This renders the $Fe^{3+}$/humic acid assembled membranes an attractive vehicle for the attachment to various kind of biocompatible layer.

Other components may also be incorporated into the bioactive polymer layer, such as poly(ethylene oxide) (PEG), to minimize protein adsorption. Poly(ethylene oxide) is most readily incorporated into the hydrogel, for example, by copolymerization of a vinyl monomer having poly(ethylene oxide) side chains, for example poly(ethylene glycol) methacrylate (which is commercially available from Aldrich Chemical Co.), or a divinyl-terminated poly(ethylene glycol) macromonomer. Copolymerization of HEMA and poly(ethylene glycol) methacrylate in the presence of AIBN yields a more flexible, unhydrated copolymer. The optimal molecular weight and content of poly(ethylene oxide) for each application can be determined by protein adsorption studies.

To provide further chemical functionality on the bioactive polymer layer, particularly a hydrogel layer, either polyvinyl alcohol or polyethylene imine may be employed as macromolecular surfactants. Where hydroxyl functionalities are available, the coupling is promoted by tresylation. Poly(ethylene oxide) may also be grafted to hydroxyl groups on the surface of the polymer layer by tresylation coupling with Jeffamine, an amine-terminated poly(ethylene oxide) commercially available from Huntsman.

In one embodiment, the biocompatible layer comprises a biocompatible membrane, which is permeable to analytes, such as oxygen and glucose, but is impermeable to, for example, white blood cells and macrophages to prevent these cells from contacting other components of the internal unit. The biocompatible membrane can comprise polymers including, but not limited to, polypropylene, polysulphone, polytetrafluoroethylene (PTFE), and poly(ethylene terephthalate) (PET). The biocompatible layer should be biostable for long periods of time (e.g., several years).

The internal unit can also comprise a mass transport-limiting layer to act as a diffusion-limiting barrier to reduce the rate of mass transport of the analyte, for example, glucose or lactate, into the internal unit. By limiting the diffusion of the analyte, the steady state concentration of the analyte in the proximity of the working electrode (which is proportional to the concentration of the analyte in the body or sample fluid) can be reduced. This extends the upper range of analyte concentrations that can still be accurately measured and can also expand the range in which the current increases approximately linearly with the level of the analyte.

In some embodiments, the mass transport limiting layer can also limit the flow of oxygen into the internal unit. This can improve the stability of internal units that are used in situations where variation in the partial pressure of oxygen causes non-linearity in internal unit response. In these embodiments, the mass transport limiting layer restricts oxygen transport by at least 40%, specifically at least 60%, and more specifically at least 80%, than the membrane restricts transport of the analyte. In these embodiments, the mass transport limiting layer comprises a film that is less permeable to oxygen, for example, by having density closer to that of the crystalline polymer, such as polyesters including polyethylene terephthalate.

FIG. 16 shows a methodology where the internal unit platform is integrated with drug delivery devices also implanted or integrated along with the internal unit.

In one embodiment, the drug delivery device delivers a tissue response modifier. "Tissue response modifiers" as used herein are factors that control the response of tissue adjacent to the site of implantation. One facet of this response can be broadly divided into a two-step process, inflammation and wound healing. An uncontrolled inflammatory response (acute or chronic) results in extensive tissue destruction and ultimately tissue fibrosis. Wound healing includes regeneration of the injured tissue, repair (fibrosis), and in-growth of new blood vessels (neovascularization and angiogenesis). For fibrosis, the body utilizes collagen from activated fibroblasts to "patch and fill" the unregenerated areas resulting from trauma and inflammation.

Fibrosis can lead to "encapsulation" or "entombment" of the sensor in fibrotic tissue and this can lead to loss of analyte supply and loss of functionality of the sensor. In-growth of new blood vessels is critical to the ultimate outcome of wound healing. A number of other responses are also included within this category, for example fibroblast formation and function, leukocyte activation, leukocyte adherence, lymphocyte activation, lymphocyte adherence, macrophage activation, macrophage adherence, thrombosis, cell migration, cell proliferation including uncontrolled growth, neoplasia, and cell injury and death. Adverse tissue responses to implantation may also arise through genetic disorders, immune diseases, infectious disease, environmental exposure to toxins, nutritional diseases, and diseases of infancy and childhood.

Tissue response modifiers are therefore a broad category of organic and inorganic, synthetic and natural materials, and derivatives thereof which affect the above responses to tissue injury upon implantation. Such materials include but are not limited to synthetic organic compounds (drugs), peptides, polypeptides, proteins, lipids, sugars, carbohydrates, certain RNA and DNA molecules, and fatty acids, as well metabolites and derivatives of each. Tissue response modifiers may also take the form of, or be available from genetic material, viruses, prokaryotic or eukaryotic cells. The tissue response modifiers can be in various forms, such as unchanged molecules, components of molecular complexes, or pharmacologically acceptable salts or simple derivatives such as esters, ethers, and amides. Tissue response modifiers may be derived from viral, microbial, fungal, plant, insect, fish, and other vertebrate sources.

Exemplary tissue response modifiers include, but are not limited to, anti-inflammatory agents such as steroidal drugs, for example corticosteroids such as Dexamethasone (9-alpha-fluoro-16-alpha-methylprednisolone), a potent, broad spectrum steroidal anti-inflammatory and anti-fibrotic drug with known efficacy in a diabetic rat model, methyl prednisone, triamcoline (fluoroxyprednilisone), hydrocortisone (17-hydroxycorticosterone); and non-steroidal drugs, for example Ketoprofin (2-(3-benzophenyl)propionic acid), cyclosporin, Naproxin ((+)-6-methoxy-alpha-methyl-2-naphthalene acetic acid), and Ibuprofin (4-isobutyl-alpha-methylphenyl acetic acid).

Other exemplary tissue response modifiers include neovascularization agents such as cytokines. Cytokines are growth factors such as transforming growth factor alpha (TGFA), epidermal growth factor (EGF), vascular endothelial growth factor (VEGF), and anti-transforming growth factor beta (TGFB). TGFA suppresses collagen synthesis and stimulates angiogenesis. It has been shown that epidermal growth factor tethered to a solid substrate retains significant mobility and an active conformation. VEGF stimulates angiogenesis, and is advantageous because it selectively promotes proliferation of endothelial cells and not fibroblasts or collagen synthesis, in contrast to other angiogenic factors. In addition to promoting would healing, the improved blood flow resulting from the presence of neovascularization agents should also improve the accuracy of sensor measurements.

Another type of tissue response modifier is a neutralizing antibody including, for example, anti-transforming growth factor beta antibody (anti-TGFB); anti-TGFB receptor antibody; and anti-fibroblast antibody (anti-CD44). Anti-TGFB antibody has been shown to inhibit fibroblast proliferation, and hence inhibit fibrosis. Because of the importance of TGFB in fibrosis, anti-TGFB receptor antibodies inhibit fibrosis by blocking TGFB activation of fibroblasts. Recent studies have demonstrated that anti-CD 44 antibody induces programmed cell death (apoptosis) in fibroblasts in vitro. Thus, use of anti-CD44 antibody represents a novel approach to inhibition of fibroblast formation, and therefore fibrosis. Other anti-proliferative agents include Mitomicyin C, which inhibits fibroblast proliferation under certain circumstances, such as after vascularization has occurred.

Adhesive ligands ("binding motifs") may also be used as tissue response modifiers, wherein the adhesive ligands are incorporated into the polymer layer to stimulate direct attachment of endothelial cells to implant surfaces. Such attachment promotes neovascularization at the implant/tissue interface. Where the surface density of binding motifs has an effect on the cellular response, variation in the density of the binding motifs allows control of the response. Exemplary adhesive ligands include but are not limited to the arginine-glycine-aspartic acid (RGD) motif, and arginine-glutamic acid-aspartic acid-valine (REDV) motif, a fibronectin polypeptide. The REDV ligand has been shown to selectively bind to human endothelial cells, but not to bind to smooth muscle cells, fibroblasts or blood platelets when used in an appropriate amount. Sensors detecting body temperature, blood gases, ionic concentrations can be incorporated in the implantable sensor platform. The analyte sensing device of claim 1, wherein the sensor element comprises a body temperature sensor, a blood pressure sensor, a pH sensor, an oxygen sensor, a glucose sensor, a lactate sensor, or a combination comprising one or more of the foregoing sensors.

In operation, the device can use any mechanism (e.g., enzymatic or non-enzymatic) by which a particular analyte can be quantitated.

The devices and methods disclosed herein can be applied to determine the metabolic levels of many analytes present in biological fluids, including, but not limited to, glucose, amino acids, and lactate. Suitable analytes include analytes that are substrates for oxidase enzymes.

Some analytes, such as oxygen, can be directly electrooxidized or electroreduced on the working electrode. For other analytes, such as glucose and lactate, an electron transfer agent and/or a catalyst can facilitate the electrooxidation or electroreduction of the analyte. Catalysts can also be used for those analytes, such as oxygen, that can be directly electrooxidized or electroreduced on the working electrode. For example, some embodiments can quantitate metabolic glucose levels by using a membrane comprising glucose oxidase (see FIG. 17) that catalyzes the conversion of glucose and molecular oxygen to gluconate and hydrogen peroxide: Glucose+$O_2$→Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration.

In one embodiment, the sensor element comprises an electrochemical pH sensor. Since a large number of biological processes are pH-dependent, there is a great need for outfitting miniaturized biosensors with a pH sensing element. The need for maintaining biocompatibility limits the use of traditional materials for the fabrication of pH-sensors (i.e., electrically semiconducting oxides such as $MoO_2$,[43] $IrO_2$,[44] or $RuO_2$[45]) due to their toxicity. Biocompatible polymers that contain nitrogen or oxygen moieties amenable to protonation have been used to develop potentiometric pH biosensors. Polyphenol, polyaniline, poly(1,2-diaminobenzene), poly(4, 4'-diaminoddiphenyl ether), etc. have been employed in fabricating pH sensors. The electrochemistry of these polymers however, is greatly affected by redox reagents (such as $H_2O_2$) and based upon prior experience with poly(o-phenyl diamine), positioning such a sensing element in the vicinity of a glucose sensor (which produces $H_2O_2$) could affect the measurements. More recently, linear polyethylenimine (L-PEI) and linear polypropylenimine (L-PPI) modified Pt electrodes have been successfully used for the development of miniaturized electrochemical pH sensors with a linear pH range from 4-9. The non-semiconducting nature of both L-PEI and L-PPI polymers render them ideal for operation within a redox-prone environment and their biocompatibility and long-term stability (when operated in a three-electrode configuration) renders them ideal for the development of our miniaturized pH sensors.

In one embodiment, ethylenediamine (EDA) or 1,3-diaminopropane (1,3-DAP) is be electropolymerized onto flat substrate by means of cyclic voltammetry in solutions composed of $10^{-2}$ M N-lithiotrifluoromethane-sulfonimide (LiTFSI) in pure EDA or 1,3-DAP, by biasing the working electrode at 3V with respect to a standard reference electrode, for a duration ranging from 5-60 min.[4] This will result in the electrodeposition of either L-PEI or L-PPI on the biased electrode, leaving the rest of the electrodes intact. Planar electrodes will be defined microlithographically. These electrodes will be grown by evaporating first a thin layer of Ti to improve adhesion on the $SiO_2$-covered Si wafer, followed by the deposition of a thick layer or Pt and an optional second thin layer of Ti to enable the adhesion of a SiN overlayer. This SiN layer is used to protect the edges of the microlithographically defined Pt electrodes from delaminating in an aqueous environment. Following SiN patterning, the remaining Ti is stripped off by immersion of the wafer in a titanium etchant (i.e., $H_2SO_4$/$H_2O$-1/1, 80° C.) to expose the underlying Pt layer.

Electroplating Ag on top of one of the patterned Pt electrode will be used to selectively grow the reference Ag/AgCl electrode. This can be accomplished by electroplating in a solution comprising KCN, $K_2CO_3$, and $KAg(CN)_2$. Subsequent electrochemical oxidation of Ag to AgCl will take place at a constant current of 40 µA (at ~0.5 V) in 0.1 M HCl for approximately 10-30 minutes Since only the reference electrode is connected to the voltage source, no deposition occurs on the other electrodes, which remain clean for the subsequent electrodeposition of L-PEI or L-PPI (described above). The use of an auxiliary Pt electrode can improve device reliability and long-term operation.

The fabrication of such a pH sensor is simple and straightforward. The thickness of the electropolymerized L-PEI or L-PPI are reported to influence the sensor response. In the case where there is interference of $H_2O_2$ with the pH sensor, this should to be quantified and included in the multi-parameter sensor response characteristics.

In one embodiment, the sensor element comprises an electrochemical oxygen sensor. Variations in the partial pressure of $O_2$ in the blood is expected to have a significant effect on the glucose sensor response. This is because of the dual role of $O_2$ in $GO_x$ enzymatic catalysis to form $H_2O_2$ and its subsequent oxidation to regenerate $O_2$. Providing an independent assessment of $O_2$ concentration could improve our level of confidence in sensor accuracy and reliability. Design simplicity, stability and good current linearity over the range of oxygen from 0 to 99.5% v/v have rendered electrochemical-based Clark sensors as the preferred method for $O_2$ sensing. A number of planar miniaturized versions of it have already been developed,[4] and variations in these are outlined below.

Planar electrodes will be defined microlithographically, as described earlier. The Pt working electrode may be covered with a biocompatible diffusion limiting membrane to control $O_2$ permeability. Fine tuning the thickness of this membrane aids in minimizing response time and maintaining sensitivity.[4] Layer-by-layer (LBL) growth of Nafion/$Fe^{3+}$ thin films allow for adjusting permeability of a variety of species. By adjusting the pH, the conformation of film growth could be tailored so as to acquire films of desired thickness. A pH of 4.5, for example, induces surface spreading of Nafion onto the substrate, thus ensuring a film growth consisting of surface spread and tightly meshed polymeric chains that exhibit high tortuosity to permeation. Moreover, the presence of $Fe^{3+}$ groups prevents the potential calcification of these films due to interactions of the negative $SO^{3-}$ groups of Nafion and the physiologically present $Ca^{2+}$ ions. This may be helpful to prevent in vivo degradation of these devices. The precise localization of such films may be performed using the well-established technique of micro-contact printing along with LBL assembly. Polyacrylamide hydrogels will be employed for the construction of these stamps, defined by crosslinking them onto lithographically etched masters. The applied force of the hydrogel on the substrate and time of contact will be adjusted accordingly.

The fabrication of this sensor is straightforward, although it requires considerable skill in terms of integrating it with the other two electrochemical sensors on the same chip. Depending on feature size, stamp micropositioning is critical. Four-degree of movement (x, y, z and tilt) stages along with corresponding controllers may be helpful in micropositioning.

In one embodiment, glucose sensor response is determined as a function of temperature, pH and oxygen. As outlined above, the interdependence of temperature, pH and oxygen content, together with various glucose levels and film-specific construction parameters create a multi-dimensional problem. A system to integrate all variables into a single calibration platform would be useful.

Standardizing all basic elements of the sensors and keeping the number of independent variables to a minimum is an objective after individual sensing functionality and longevity are established. This will be followed by conducting a series of calibrations.

TABLE I

Typical Glucose sensor voltages

| Sensor | $V_{REF}$ | $V_{Working}$ | Type |
|---|---|---|---|
| $CO_2$ | Sensor specific | Sensor specific | Electrochem |
| Ionic | Sensor specific | Sensor specific | Electrochem |
| Glucose | 0.7 V | 1.2 V | Electrochem |

The invention claimed is:

1. An analyte sensing device comprising:
an external control unit and an implantable sensor platform in wireless optical two-way operable communication, wherein the implantable sensor platform can pass though a 14 gauge or smaller bore needle,
wherein the implantable sensor platform comprises, in operable communication,
a photovoltaic device to receive optical power from the external control unit to serve as a power source for powering said implantable sensor platform,
an optical receiver for detecting signals produced by the external control unit,
an electrical to optical converter,
a plurality of sensor elements deposited on a surface of the implantable sensor platform and operable for sensing one or more analytes,
wherein the plurality of sensor elements have one or more working electrodes, a reference electrode and a counter electrode the surface of the implantable sensor platform deposited on such that the one or more working electrodes, the reference electrode, and the counter electrode do not delaminate when exposed to body fluids,
an interfacing circuit, for providing operating parameters to the electrodes of the plurality of sensor elements and controlled feedback for the operation of the plurality of sensor elements, wherein the plurality of sensor elements generates a sensor output signal having a sensor output signal magnitude proportional to the amount of analyte present,
wherein the interfacing circuit comprises at least one potentiostat,
a signal processing circuit interfaced with the sensor output signal, wherein the signal processing circuit converts the sensor output signal of the plurality of sensor elements to digital pulses having a pulse frequency,
wherein the pulse frequency is determined by the sensor output signal magnitude and wherein changes in the pulse frequency are proportional to changes in the analyte levels, wherein the electrical to optical converter converts the digital pulses to optical pulses and transmits the optical pulses to the external control unit,
a switching mode selector configured to cause the implantable sensor platform to perform at least one of an initialization function, a power level check function, a potentiostat circuit reconfiguration function for analyte level measurement, an implantable sensor selection function, and an implantable sensor calibration function,
one or more optical components for facilitating wavelength selection, transmission and/or reflection, and
a biocompatible coating surrounding at least a portion of the implantable sensor platform,
wherein said biocompatible coating comprises a drug and is designed to control the timed release of the drug,
wherein the external control unit comprises, in operable communication,
an optical source suitable for powering the photovoltaic device of the implantable sensor platform,
an optical receiver suitable for receiving one or more optical pulses from the implantable sensor platform and converting the optical pulses to electrical pulses,
an optical transmitter suitable to transmit one or more optical pulses to the optical receiver of the implantable sensor platform, wherein the optical pulse relays instructions to the switching mode selector to cause the implantable sensor platform to perform at least one of the initialization function, the power level check function, the potentiostat circuit reconfiguration function, the sensor selection for analyte level measurement function, the implantable sensor selection function and the implantable sensor calibration function,
wherein the wavelength of the optical receiver is different from the wavelength of the optical transmitter in the external control unit,
an integrated circuit for processing and displaying the electrical pulses, wherein the integrated circuit is in operable communication with the optical receivers,
a microcontroller comprising a program code, programmable memory, and means to display output and communicate with other devices, means of interfacing with the optical source, optical receivers and optical transmitters, to establish an operable communication with the implantable sensor platform,
a power supply to power the external unit,
one or more optical components providing wavelength selection, transmission or reflection functions, and
a miniaturized camera to align the implantable sensor platform with the optical components of the external control unit.

2. The analyte sensing device of claim 1, wherein the implantable sensor platform comprises three sub-chips in operable communication, wherein
sub-chip #1 comprises
the photovoltaic device,
an optical transmitter for transmitting information in the form of optical pulses to the external unit, and
the optical receiver;
sub-chip #2 comprises
the interfacing circuit including initialization circuits, sensor select circuits, and sensor calibration circuits,
the potentiostat and signal processing circuit,
the electrical to optical converter; and
sub-chip #3 comprises the plurality of sensor elements.

3. The analyte sensing device of claim 2, wherein the three sub-chips are integrated with interconnects.

4. The analyte sensing device of claim 1, wherein the interfacing circuit comprises a voltage control logic unit, the signal processing circuit comprises a potentiostat, and the electrical to optical converter comprises an analog to digital converter.

5. The analyte sensing device claim 1, wherein the plurality of sensor elements monitor a plurality of analytes.

6. The analyte sensing device of claim 5, wherein the switching mode selector sequentially addresses the plurality of sensor elements.

7. The analyte sensing device of claim 1, wherein the plurality of sensor elements includes at least one of a body temperature sensor, a blood pressure sensor, a pH sensor, an oxygen sensor, a glucose sensor, and a lactate sensor.

8. The analyte sensing device of claim 1, further comprising a feedback system between the implantable sensor platform and the external control unit.

9. The analyte sensing device of claim 1, wherein the biocompatible coating is a hydrogel.

10. The analyte sensing device of claim 1, wherein the biocompatible coating comprises an agent to suppress and control inflammation, an agent to suppress and control fibrosis, an antibiotic, an agent to prevent and control infection, an agent to promote angiogenesis, an agent to maturate blood vessels encapsulated, or a combination of two or more of the foregoing agents.

11. The analyte sensing device of claim 10, wherein the agent to suppress and control inflammation or fibrosis comprises dexamethasone, ibuprofen, triamcinalone, mitomycin C, anti-fibroblast antibody (anti-CD44), anti-transforming growth factor-β (anti-TGF-β) receptor antibody, or transforming growth factor-a (TGF-a).

12. The analyte sensing device of claim 11, wherein the agent is provided by a gene therapeutic.

13. The analyte sensing device of claim 10, wherein the agent to promote angiogenesis and blood vessel maturation agents comprise vascular endothelial growth factor (VEGF), transforming growth factor-a (TGF-a), anti-thrombospondin-2, or platelet derived growth factor PDGF.

14. The analyte sensing device of claim 10, wherein the antibiotic comprises Amikacin, Gentamycin, Kanamycin, Neomycin, Netilmicin, Paromomycin, Streptomycin, Tobramycin, Ertapenem, Imipenem, Meropenem, Chloramphenicol, Ciprofloxacin, Gatifloxacin, Gemifloxacin, Grepafloxacin, Levofloxacin, Lomefloxacin, Moxifloxacin, Norfloxacin, Ofloxacin, Sparfloxacin, Trovafloxacin, Vancomycin; Clindamycin; Azithromycin, Clarithromycin, Dirithromycin, Erythromycin, Telithromycin, Cefadroxil, Cefazolin, Cephalexin, Cephalothin, Cephapirin, Cephradine, Cefaclor, Cefamandole, Cefonicid, Cefotetan, Cefoxitin, Cefprozil, Cefuroxime, Loracarbef, Cefdinir, Cefditoren, Cefixime, Cefoperazone, Cefotaxime, Cefpodoxime, Ceftazidime, Ceftibuten, Ceftizoxime, Ceftriaxone, Cefepime, Aztreonam, Metronidazole, Linezolid, Amoxicillin, Amoxicillin/Clavulanate, Ampicillin, Ampicillin/Sulbactam, Bacampicillin, Carbenicillin, Cloxacillin, Dicloxacillin, Methicillin, Mezlocillin, Nafcillin, Oxacillin, Penicillin G, Penicillin V, Piperacillin, Piperacillin/Tazobactam, Ticarcillin, Ticarcillin/Clavulanate, Quinupristin, Dalfopristin, Sulfamethoxazole/Trimethoprim, Demeclocycline, Doxycycline, Minocycline, Tetracycline, or a combination of one or more of the foregoing antibiotics.

15. The analyte sensing device of claim 1, wherein the drug delivery device is selected from microspheres, nanoparticles, liposomes, lipid complexes, micelles, or a combination of two or more of the foregoing drug delivery devices.

16. The analyte sensing device of claim 15, wherein the microspheres comprise a polymer selected from polylactide (PLA), polyglycolide (PGA), lactide-glycolide copolymers (PLGA), polycaprolactone, lactide-caprolactone copolymers, polyhydroxybutyrate, polyalkylcyanoacrylates, polyanhydrides, polyorthoesters, albumin, collagen, gelatin, dextrans, starches, acrylate polymers, methyl methacrylate, methacrylic acid, hydroxyalkyl acrylates, methacrylates, methylene glycol dimethacrylate, acrylamide, bisacrylamide, cellulose-based polymers, ethylene glycol polymers, ethylene glycol copolymers, oxyethylene, oxypropylene polymers, poly(vinyl alcohol), polyvinylacetate, polyvinylpyrrolidone, polyvinylpyridine or a combination of two or more of the foregoing polymers.

17. The analyte sensing device of claim 15, wherein the nanoparticles are copolymers of PLGA and PEG.

18. The analyte sensing device of claim 15, wherein the lipid comprises 1,2-Dilauroyl-sn-Glycero-3-Phosphocholine (DLPC); 1,2-Dimyristoyl-sn-Glycero-3-Phosphocholine (DMPC); 1,2-Dipalmitoyl-sn-Glycero-3-Phosphocholine (DPPC); 1,2-Distearoyl-sn-Glycero-3-Phosphocholine (DSPC); 1,2-Dioleoyl-sn-Glycero-3-Phosphocholine (DOPC); 1,2-Dimyristoyl-sn-Glycero-3-Phosphoethanolamine (DMPE); 1,2-Dipalmitoyl-sn-Glycero-3-Phosphoethanolamine (DPPE); 1,2-Dioleoyl-sn-Glycero-3-Phosphoethanolamine (DOPE); 1,2-Dimyristoyl-sn-Glycero-3-Phosphate (Monosodium Salt) (DMPA); 1,2-Dipalmitoyl-sn-Glycero-3-Phosphate (Monosodium Salt) (DPPA); 1,2-Dioleoyl-sn-Glycero-3-Phosphate (Monosodium Salt) (DOPA); 1,2-Dimyristoyl-sn-Glycero-3-[Phospho-rac-(1-glycerol)] (Sodium Salt) (DMPG); 1,2-Dipalmitoyl-sn-Glycero-3-[Phospho-rac-(1-glycerol)] (Sodium Salt) (DPPG); 1,2-Dioleoyl-sn-Glycero-3-[Phospho-rac-(1-glycerol)] (Sodium Salt) (DOPG); 1,2-Dimyristoyl-sn-Glycero-3-[Phospho-L-Serine] (Sodium Salt) (DMPS); 1,2-Dipalmitoyl-sn-Glycero-3-[Phospho-L-Serine] (Sodium Salt) (DPPS); 1,2-Dioleoyl-sn-Glycero-3-[Phospho-L-Serine] (Sodium Salt) (DOPS); 1,2-Dioleoyl-sn-Glycero-3-Phosphoethanolamine-N-(glutaryl) (Sodium Salt); 1,1',2,2'-Tetramyristoyl Cardiolipin (Ammonium Salt); 1,2-Dipalmitoyl-sn-Glycero-3-Phosphoethanolamine-N-[Methoxy(Polyethylene glycol)-2000] (Ammonium Salt); 1,2-Dipalmitoyl-sn-Glycero-3-Phosphoethanolamine-N-[Methoxy(Polyethylene glycol)-5000] (Ammonium Salt); 1,2-Dioleoyl-3-Trimethylammonium-Propane (Chloride Salt) (DOTAP), cholesterol, or a combination of two or more of the foregoing lipids.

19. The analyte sensing device of claim 9, wherein the hydrogel comprises anionic polymers; cationic polymers; amphipathic polymers; neutral polymers, synthetic polymers, or a combination of two or more of the foregoing polymers.

20. The analyte sensing device of claim 1, comprising a Pt working electrode comprising a Au/Ti/Pt layer or a Au/Ti/Pt/Ti/Ag layer.

21. The analyte sensing device of claim 2, wherein each of the sub-chips comprises a silicon circuit, a silicon-oxide coated light emitting diode and a silicon-oxide coated photodetecting device.

22. The analyte sensing device of claim 2, wherein the optical transmitters, receiver and photovoltaic device operate at different optical wavelengths to avoid interference and optimize their respective performance.

23. The analyte sensing device of claim 1, wherein the implantable sensor platform includes an ultrasound transmitter that converts the digital electrical pulses into ultrasound pulses and transmits the ultrasound pulses to the external control unit.

24. The analyte sensing device of claim 1, wherein the device is designed to operate in manner which accepts various coding schemes for selecting at least one of the plurality of sensor elements, the calibration function, initialization function, and the power level check function.

25. A method of using the analyte sensing device of claim 1, comprising subcutaneously implanting the implantable sensor platform.

26. The method of claim 25, wherein the implantable sensor platform is implanted using a 14 gauge or smaller needle.

27. The analyte sensing device of claim 1, wherein the external control unit is capable of continuous monitoring of the level of an analyte within a host, and
wherein the device comprises a feedback system between the implantable sensor platform and the external control unit.

28. The analyte sensing device of claim 27, wherein the feedback system has a function selected from verifying power levels in the implantable device, adjusting sensor calibration, selecting a sensor for data retrieval, or a combination comprising one or more of the foregoing functions.

29. A method of monitoring an analyte level in a host, comprising providing the analyte sensing device of claim 1;
determining the metabolic level of the analyte in a host;
transmitting a signal proportional to a metabolic level of the analyte to the external unit; and
displaying information regarding the metabolic level of the analyte on the external control unit.

30. The analyte sensing device of claim 1, wherein if the sensor output signal is a current signal, the current signal is converted by the signal processing circuit into a voltage signal,
wherein the voltage signal is converted into an RF signal whose frequency is proportional to the analyte level, and which is wirelessly transmitted using an antenna on a subchip
to an electronic receiver located in the external control unit.

31. The analyte sensing device of claim 1, wherein the implantable sensor platform comprises two sub-chips in operable communication, wherein
sub-chip #1 comprises
the photovoltaic device, a first photodetector for power monitoring, and a second photodetector for a function selected from initialization, sensor selection, control feedback, calibration of sensors, and potentiostat voltage check; and
sub-chip #2 comprises
the interfacing circuit, the signal processing circuit, the electrical to optical converter, a calibration and initializing circuit; and the plurality of sensor elements,
wherein sub-chip #1 is hermetically sealed; and wherein a portion of sub-chip 2 is hermetically sealed in a manner such that the sensor electrodes are exposed to body fluids.

32. The analyte sensing device of claim 1, wherein a sensor output current signal is converted into an electronic voltage signal which drives an ultrasound transducer, and the ultrasound produced by the ultrasound transducer is received by a receiver located in the external control unit.

33. An analyte sensing device comprising:
an external control unit and an implantable sensor platform in wireless optical two-way operable communication, wherein the implantable sensor platform can pass though a 14 gauge or smaller bore needle,
wherein the implantable sensor platform comprises sub-chip #1, sub-chip #2 and sub-chip#3 and a biocompatible coating surrounding at least a portion of the implantable sensor platform,
wherein sub-chip #1 comprises:
a photovoltaic device that powers the sub-chip #1, sub-chip #2 and sub-chip#3,
a first optical receiver to receive instructions from a mode select unit located in the external control unit via an external unit optical transmitter, wherein the external unit optical transmitter is located in the external control unit, and
a second optical receiver for providing information regarding light intensity received from light-emitting diodes located in the external control unit;
wherein the first and second optical receivers operate at wavelengths such that the first and second optical receivers do not interfere with each other,
a sensor platform optical transmitter configured to transmit an optical signal having a wavelength of in the range of 1.3 to 1.55 microns, relaying information selected from sensor output, calibration, potentiostat check, or solar power level check received from a driver located on subchip#2,
one or more coatings providing wavelength selection, transmission or reflection functions,
wherein sub-chip #2 comprises:
a plurality of interfacing circuits selected from initialization circuits, sensor select circuits, and sensor calibration circuits,
a potentiostat,
a signal processing circuit,
a logic circuit, a demultiplexer, a multiplexer, and the driver to enable transmission of feedback signals selected from a level of radiation intensity received by the photovoltaic device, a reference voltage of the potentiostat, or a sensor reading, and
wherein the driver on subchip#2 transmits a plurality of pulses to the sensor platform optical transmitter located on subchip#1 and transmits using 1.3-1.55 micron optical wavelengths, and wherein the sensor platform optical transmitter does not interfere with the light emitting diodes and the external unit optical transmitter,
wherein sub-chip #3 comprises a plurality of sensor elements operable for sensing of one or more analytes,
and wherein the plurality of sensor elements has one or more working electrodes, a reference electrode and a counter electrode, wherein the one or more working electrodes, reference electrode and counter electrodes are in contact with the surface they are deposited on in a way that they do not delaminate when exposed to body fluids,
wherein the plurality of sensor elements are in contact with the potentiostat and other circuits located on subchip #2,
wherein sub-chip #1, sub-chip #2 and sub-chip#3 are electrically interconnected and integrated in a manner to operate in the presence of body fluids;
wherein the external control unit comprises, in operable communication, an optical source comprising light-emitting diodes and laser diodes, wherein the optical source powers the photovoltaic device on sub-chip #1,
a third optical receiver for receiving one or more optical pulses having a wavelength in the range of 1.3-1.55 micron from the sensor platform optical transmitter on subchip#1 of the implantable sensor platform,
wherein the signal processing circuit converts a sensor element output signal to digital pulses,
wherein the sensor platform optical transmitter converts the digital pulses to optical pulses,
wherein the frequency of the optical pulses is determined by the sensor element output signal which is controlled by an analyte level in the body fluids,
wherein the external unit optical transmitter transmits one or more optical pulses to the first optical receiver, wherein the one or more optical pulse relays instructions to sub-chip #2 for the switching, multiplexing, demultiplexing and logic circuits of sub-chip #2 to provide at least one function wherein the at least one function includes an initialization function, a power check function, a potentiostat circuit reconfiguration for analyte level measurement function, an implantable sensor selection function, and an implantable sensor calibration function, an integrated circuit for processing and displaying an electrical pulse, wherein the integrated circuit is in operable communication with an optical receiver, a microcontroller comprising a program code; programmable memory; a means to display the output and communicate with other devices; a means of interfacing with the optical source, an optical receiver located in the external control unit operating at 1.3 to 1.55 microns and an optical transmitter located in the external control unit operating at 800-1000 nanometers, a power supply to power the external control unit, one or more optical components providing wavelength selection, transmission, or reflection functions, and a miniaturized camera to align the implantable sensor platform with the optical components of the external control unit.

34. The analyte sensing device of claim 33, wherein
the external control unit is configured to transmit an optical signal to the implantable sensor platform at a wavelength range of 800-1000 nanometers, and
wherein the implantable sensor platform is configured to transmit an optical signal to the external control unit at a wavelength range of 1.3-1.55 microns.

35. The analyte sensing device of claim 33 wherein the sensor platform optical transmitter operating at a range of 1.3-1.55 micron located on subchip#2 is located proximate to the driver circuit providing information selected from the initialization function, the power check function, the potentiostat circuit reconfiguration function, the sensor selection for analyte level measurement function, and the sensor calibration function.

36. The analyte sensing device of claim 33, wherein the plurality of sensor elements comprise a body temperature sensor, a blood pressure sensor, a pH sensor, an oxygen sensor, a glucose sensor, a lactate sensor, or a combination of two or more of the foregoing sensors.

37. An implantable biosensor platform for sensing an analyte in a host, wherein the implantable biosensor is configured to operate with an external control unit, the implantable biosensor platform comprising:

a photovoltaic device (PV), configured to receive power source light from the external control unit and convert the power source light into electricity used to power the implantable biosensor, wherein the power source light operates at a first wavelength;

a plurality of electrodes, wherein at least one of the plurality of electrodes is configured to be exposed to the analyte to measure analyte levels;

a first photodetector ($PD_m$) configured to receive the power source light and generate input power level information responsive to the power source light;

control circuitry configured to receive and compare the input power level information with a power reference level;

a second photodetector ($PD_{SS}$) configured to receive an optical control information signal from the external control unit, wherein the optical control information signal has a second wavelength; and processing circuitry configured to receive an electrical signal from at least one of the plurality of electrodes and convert the electrical signal into a digital signal which includes digital pulses whose frequency varies responsive to the electrical signal; and a transmitter ($TX_D$) in signal communication with the processing circuitry and configured to optically transmit the digital signal to the external control unit, wherein the optical signal is transmitted via a third wavelength, wherein the first wavelength, second wavelength and third wavelength differ from each other.

38. An analyte sensing device, comprising:

a sensor platform configured to be implantable within a living body having body fluids by passing through the bore of a needle, wherein the sensor platform is encapsulated in a biocompatible coating and comprises, a plurality of sensor elements each having a sensor surface, wherein when the sensor platform is located within the living body and the sensor surface is in contact with body fluid, the plurality of sensor elements generate a sensor output signal having a sensor output signal magnitude proportional to the concentration of the one or more analytes, a photovoltaic device (PV) configured to operate in response to electromagnetic energy from an external control unit optical power source and generate PV electrical output power for powering the sensor platform, wherein the sensor platform includes a sensor platform mode selector connected to,
a multiplexer (MUX),
a demultiplexer (DEMUX), and
a logic circuit configured to perform,
an initialization function,
a power level check function,
a potentiostat circuit reconfiguration function,
a sensor selection function for measuring an analyte level, and
a sensor calibration function, and a first optical receiver configured to operate at a $1^{st}$ wavelength for detecting coded optical pulses produced by an external control unit optical transmitter, a potentiostat in operable communication with the plurality of sensor elements, wherein the potentiostat is configured to provide operating parameters to one or more of the plurality of sensor elements, a signal processing circuit configured to receive the sensor output signal and convert the sensor output signal into electrical digital pulses having a pulse frequency, wherein the pulse frequency is responsive to the sensor output signal magnitude such that changes in the pulse frequency are proportional to changes in the concentration of the one or more analytes, a sensor platform optical transmitter configured to operate at a $2^{nd}$ wavelength to receive electrical digital pulses and convert the electrical digital pulses to optical digital pulses and transmit the optical digital pulses to an external control unit optical receiver, wherein the $2^{nd}$ wavelength is not equal to the $1^{st}$ wavelength, a $2^{nd}$ optical receiver connected to the sensor platform mode selector and configured to receive electromagnetic energy from the external control unit optical power source and cause the sensor platform mode selector to send a signal to the external control unit via the sensor platform optical transmitter if the electromagnetic energy from the external control unit optical power source is above a threshold voltage.

39. An analyte sensing device for implantation into a living body via the bore of a needle, wherein the analyte sensing device is encapsulated in a biocompatible coating, the analyte sensing device comprising:

at least one sensor element each having a sensor surface for sensing one or more analytes, wherein when the sensor platform is located within the living body and the sensor surface is in contact with body fluid, the at least one sensor element generates a sensor output signal having a sensor output signal magnitude proportional to the concentration of the one or more analytes, a photovoltaic device (PV) configured to operate responsive to electromagnetic energy from an external control unit optical power source and generate PV electrical output power for powering the analyte sensing device, a sensor platform mode selector, a first optical receiver configured to operate at a $1^{st}$ wavelength for detecting coded optical pulses produced by an external control unit optical transmitter, a potentiostat in operable communication with the at least one sensor element, wherein the potentiostat is configured to provide operating parameters to the at least one sensor element, a signal processing circuit configured to receive the sensor output signal and convert the sensor output signal into electrical digital pulses having a pulse frequency, wherein the pulse frequency is responsive to the sensor output signal magnitude such that changes in the pulse frequency are proportional to changes in the concentration of the one or more analytes, a sensor platform optical transmitter configured to operate at a $2^{nd}$ wavelength to receive electrical digital pulses and convert the electrical digital pulses to optical digital pulses and transmit the optical digital pulses to an external control unit optical receiver, wherein the $2^{nd}$ wavelength is not equal to the $1^{st}$ wavelength, and a $2^{nd}$ optical receiver configured to operate responsive to the electromagnetic energy to cause the sensor platform mode selector to send a signal to the external control unit via the sensor platform optical transmitter if the electromagnetic energy is above a threshold voltage.

40. The analyte sensing device of claim 39, further including, a multiplexer (MUX),
a demultiplexer (DEMUX), and
a logic circuit configured to perform,
  an initialization function,
  a power level check function,
  a potentiostat circuit reconfiguration function,
  a sensor selection function for measuring an analyte level, and
  a sensor calibration function,
wherein the MUX, DEMUX and logic circuit are connected to the sensor platform mode selector.

* * * * *